(12) United States Patent
Kurzchalia et al.

(10) Patent No.: US 10,434,077 B2
(45) Date of Patent: Oct. 8, 2019

(54) GLYCOLIC ACID AND/OR D-LACTIC ACID FOR THE TREATMENT OF NEURODEGENERATIVE DISEASES

(71) Applicant: MAX-PLANCK-GESELLSCHAFT ZUR FOERDERUNG DER WISSENSCHAFTEN E.V., Munich (DE)

(72) Inventors: Teymuras Kurzchalia, Berlin (DE); Anthony A Hyman, Dresden (DE); Yusuke Toyoda, Dresden (DE); Francisco Pan-Montojo, Dresden (DE); Cihan Erkut, Dresden (DE)

(73) Assignee: MAX-PLANCK-GESELLSCHAFT ZUR FÖRDERUNG DER WISSENSCHAFTEN E.V., München (DE)

( * ) Notice: Subject to any disclaimer, the term of this patent is extended or adjusted under 35 U.S.C. 154(b) by 339 days.

(21) Appl. No.: 15/532,930

(22) PCT Filed: Mar. 31, 2015

(86) PCT No.: PCT/EP2015/057023
§ 371 (c)(1),
(2) Date: Jun. 2, 2017

(87) PCT Pub. No.: WO2015/150383
PCT Pub. Date: Oct. 8, 2015

(65) Prior Publication Data
US 2017/0326085 A1    Nov. 16, 2017

(30) Foreign Application Priority Data
Mar. 31, 2014   (EP) ..................... 14162874

(51) Int. Cl.
| | | |
|---|---|---|
| A61K 31/19 | (2006.01) | |
| A23C 9/152 | (2006.01) | |
| A23L 33/00 | (2016.01) | |
| A23L 33/10 | (2016.01) | |
| A23L 33/15 | (2016.01) | |
| A61K 31/122 | (2006.01) | |
| A61K 45/06 | (2006.01) | |

(52) U.S. Cl.
CPC .............. *A61K 31/19* (2013.01); *A23C 9/152* (2013.01); *A23L 33/10* (2016.08); *A23L 33/15* (2016.08); *A23L 33/30* (2016.08); *A61K 31/122* (2013.01); *A61K 45/06* (2013.01); *A23V 2002/00* (2013.01)

(58) Field of Classification Search
CPC .......... A23L 33/10; A23L 33/15; A23L 33/30; A61K 31/122; A61K 45/06; A61K 31/19; A61K 2300/00; A23C 9/152; A23V 2002/00
See application file for complete search history.

(56) References Cited

U.S. PATENT DOCUMENTS

| | | | |
|---|---|---|---|
| 4,360,523 A | 11/1982 | Kaplan | |
| 5,547,988 A | 8/1996 | Yu et al. | |
| 5,767,163 A | 6/1998 | Kundsin | |
| 2002/0049182 A1* | 4/2002 | Von Borstel | ......... A61K 31/197 514/44 R |
| 2007/0203080 A1* | 8/2007 | Lipshutz | ............... C07C 37/055 514/34 |
| 2008/0233263 A1* | 9/2008 | Coy | ..................... A23C 9/1315 426/592 |
| 2012/0283328 A1 | 11/2012 | Modi | |
| 2013/0202659 A1* | 8/2013 | Crawford | ............... A61K 47/60 424/400 |

OTHER PUBLICATIONS

English International Search Report dated Mar. 31, 2015 by the European Patent Office in International Application PCT/EP2015/057023.
Parikh Sumit et al:"A modern approach to the treatment of mitochondrial disease." Current Treatment Options in Neurology Nov. 2009; vol. 11, No. 6, Nov. 2009(Nov. 2009), pp. 414-430.
Hanstock T L et al:"Increased plasma d-lactic acid associated with impaired memory in rats", Physiology and Behavior, Elsevier Science Ltd.,Oxford, GB, vol. 101, No. 5, Dec. 2, 2010(Dec. 2, 2010), pp. 653-659, Abstract only.
Ling Binbing et al: "D-Lactate altered mitochondrial energy production in rat brain and heart but not liver.", Nutrition & Metabolism 2012, vol. 9, No. 1, 2012, p. 6.
Cox J A et al: "Excitatory amino acid neurotoxicity at the N-methyl-d-aspartate receptor in cultured neurons:role of the voltage-dependent magnesium block", Brain Research, Elsevier, Amsterdam, NL, vol. 499, No. 2, Oct. 16, 1989 (Oct. 16, 1989), pp. 267-272, Abstract only.
Lin Michael T et al:"Mitochondrial dysfunction and oxidative stress in neurodegenerative diseases", Nature, Nature Publishing Group, United Kingdom, vol. 443, No. 7113, Oct. 19, 2006 (Oct. 19, 2006), pp. 787-795, Abstract only.
Lee Ju-Young et al: "Human DJ-1 and its homologs are novel glyoxalases.", Human Molecular Genetics 15. Jul. 2012, vol. 21, No. 14, Jul. 15, 2012( Jul. 15, 2012).
Facecchia Katie et al:"Oxidative toxicity in neurodegenerative diseases:role of mitochondrial dysfunction and therapeutic strategies.", Journal of Toxicology 2011, vol. 2011, 2011, p. 683728.
Di Mauro Salvatore et al"Mitochondrial disorders in the nervous system.", Annual Review of Neuroscience 2008, vol. 31, 2008, pp. 91-123, Abstract only.
Aubert-Pouëssel, A. et al. ,,In vitro study of GDNF release from biodegradable PLGA microspheres, Journal of Controlled Release 95, (2004), pp. 463-475.

(Continued)

*Primary Examiner* — Doan T Phan
(74) *Attorney, Agent, or Firm* — Ursula B. Day

(57) ABSTRACT

A method of treatment of a neurodegenerative disease which is associated with a decline in mitochondrial activity, includes administering to a person in need of such treatment at least one of Glycolic acid or a pharmaceutically acceptable salt or ester thereof, and D-lactic acid or a pharmaceutically acceptable salt or ester thereof.

12 Claims, 12 Drawing Sheets
Specification includes a Sequence Listing.

(56) References Cited

OTHER PUBLICATIONS

Bowen, B. C. et al. "Proton MR Spectroscopy of the Brain in 14 Patients with Parkinson Disease", ANJR, 16 (1995), pp. 61-68.

Chen H. & Chan D. "Mitochondrial dynamics—fusion, fission, movement, and mitophagy—in neurodegenerative diseases", Human Molecular Genetics, vol. 19, 2, (2009), R169-R176.

Di Monte D. et al "Blood Lactate in Parkinson's Disease", Annals of Neurology, vol. 29, No. 3, (1991), p. 342.

Fadieieva, A. & Grechanina, Y. "Investigation of association between change of blood lactic acid and biochemical indexes in patients with clinical signs of mitochondrial dysfunction" Abstracts/ Clinical Biochemistry 44 (2011) pp. 529-530.

Gårseth M. et al. "Proton Magnetic Resonance Spectroscopy of Cerebrospinal Fluid in Neurodegenerative Disease: Indication of Glial Energy Impairment in Huntington Chorea, but Not in Parkinson Disease", Journal of Neuroscience Research 60, (2000), pp. 779-782.

Kang, P. B. et al. „Lactic Acid Elevation in Extramitochondrial Childhood Neurodegenerative Diseases, Journal of Child Neurology, vol. 16, No. 9, (2001) pp. 657-660.

Shin, M. et al. "Dopamine-Loaded Poly($_{D,L}$-lactice-co-glyocolic acid) Microspheres: New Strategy for Encapsulating Small Hydrophilic Drugs with High Efficiency", Biotechnol. Prog., vol. 30, No. 1 (2014), pp. 215-223.

Tiwari, M. N. et al. „Nicotine-encapsulated poly(lactic-co-glycolic) acid nanoparticles improve neuroprotective efficacy against MPTP-induced parkinsonism, Free Radical Biology and Medicine 65, (2013), pp. 704-718.

Yates, C. M. et al. "Enzyme Activities in Relation to pH and Lactate in Postmortem Brain in Alzheimer-Type and Other Dementias", Journal of Neurochemistry, vol. 55, No. 5, (1990), pp. 1624-1630.

\* cited by examiner

Figure 3
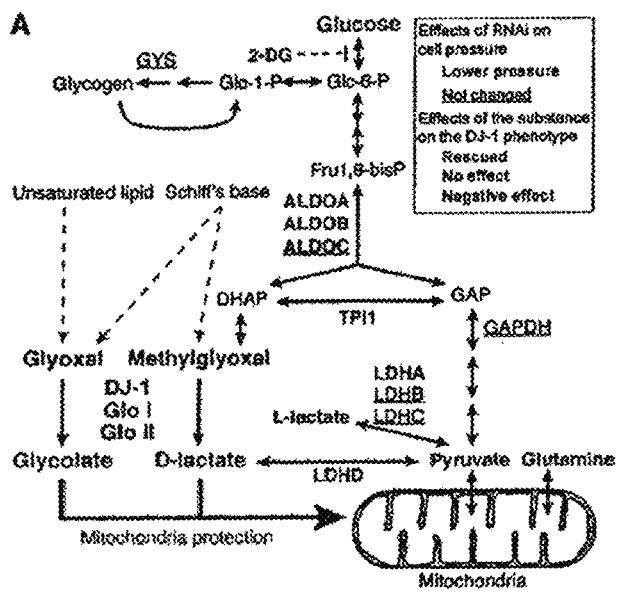
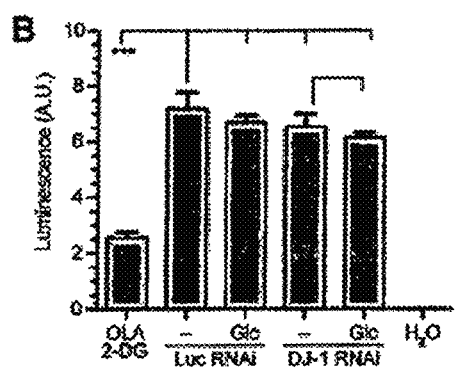
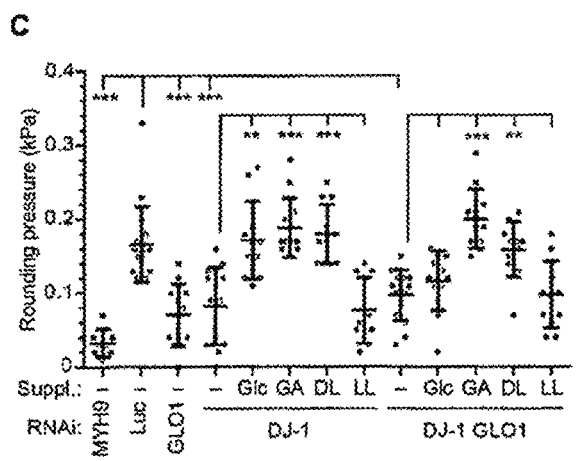

Figure 5
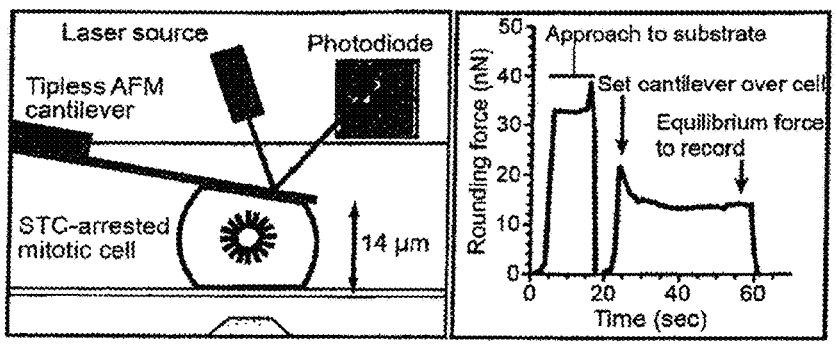
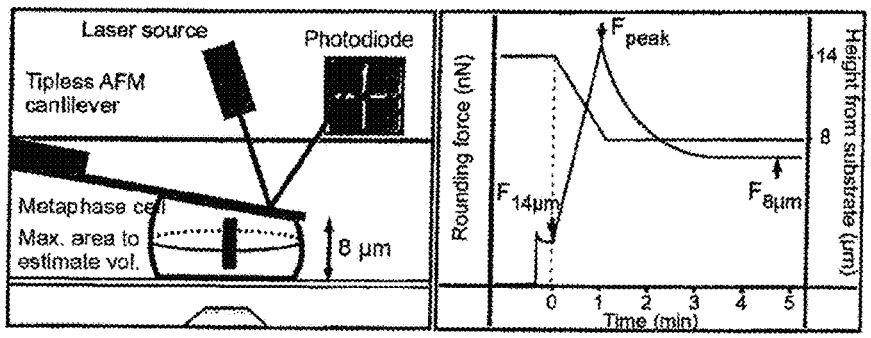
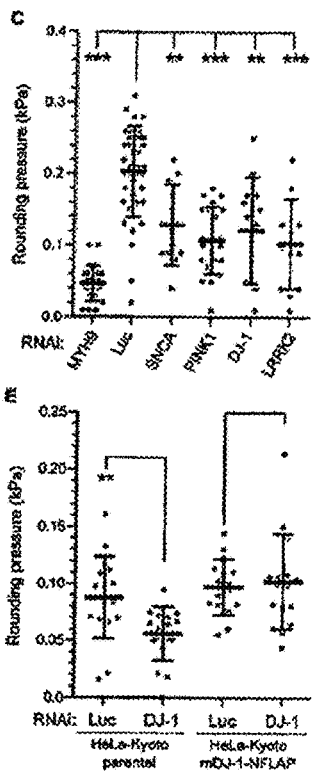
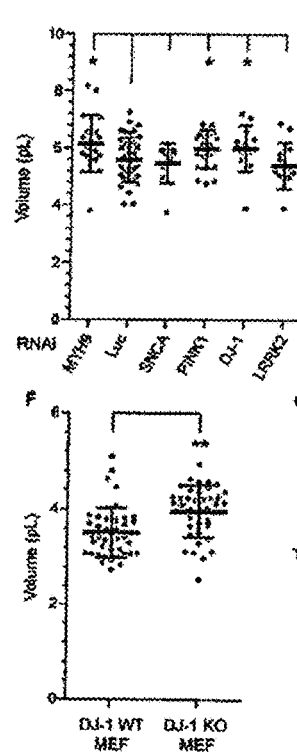
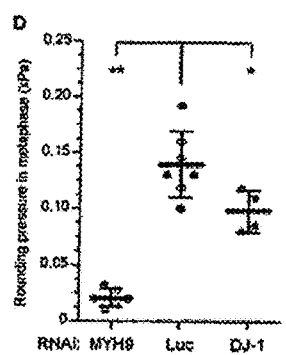
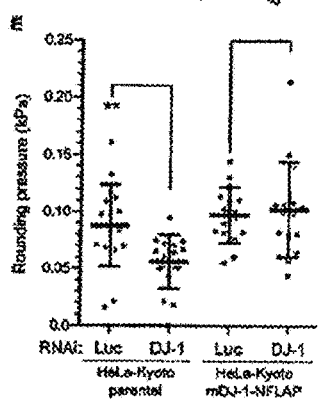
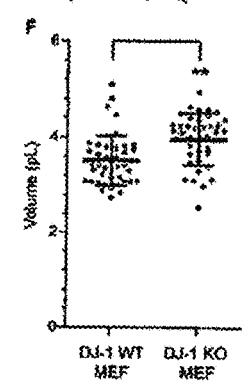
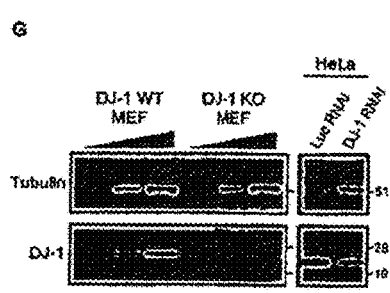

Figure 11
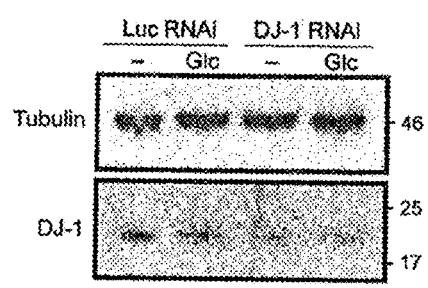
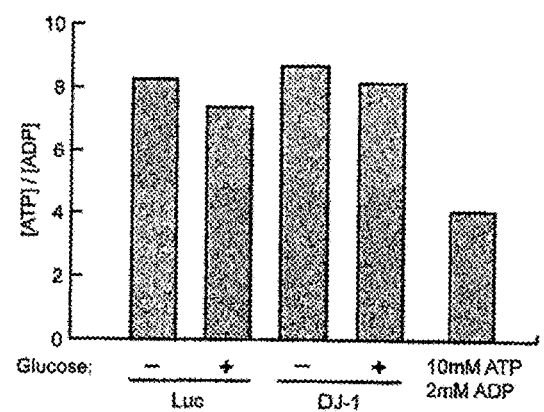
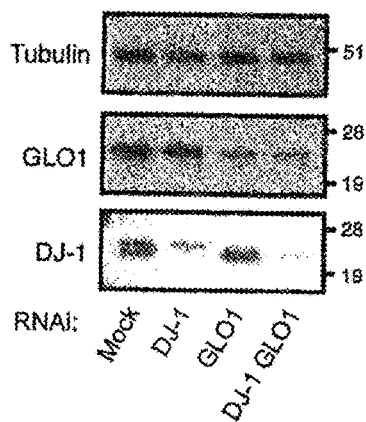
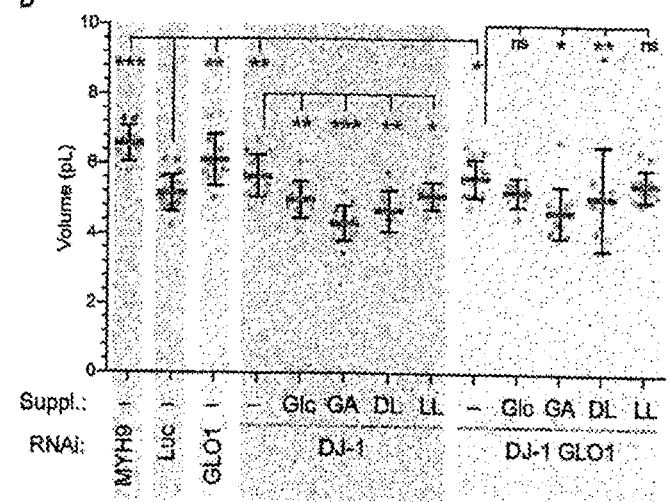

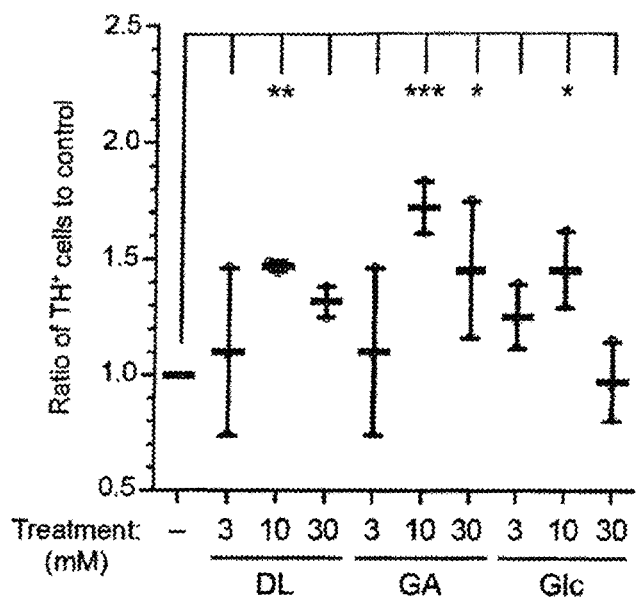

B

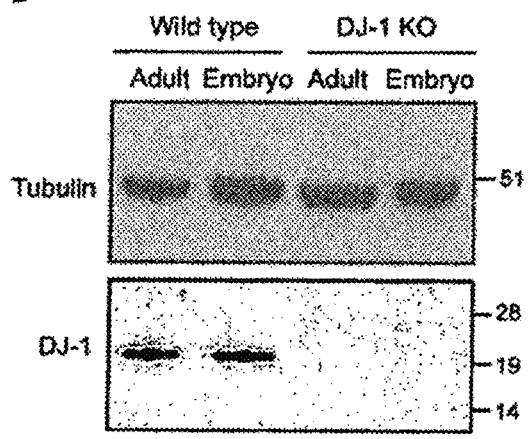

Figure 13

| Target gene | Pressure of RNAi cells (kPa) | Relative pressure to Luc control | Effect on mitotic cell pressure |
|---|---|---|---|
| GYS1 + GYS2 | 0.24 ± 0.040 | 0.92 | No phenotype |
| ALDOA | 0.14 ± 0.051 | 0.76 | Lower pressure |
| ALDOB | 0.086 ± 0.045 | 0.44 | Lower pressure |
| ALDOC | 0.19 ± 0.058 | 0.97 | No phenotype |
| TPI1 | 0.13 ± 0.044 | 0.70 | Lower pressure |
| GAPDH | 0.19 ± 0.039 | 0.96 | No phenotype |
| GLO1 | 0.15 ± 0.044 | 0.71 | Lower pressure |
| HAGH/GLO2 | 0.16 ± 0.039 | 0.75 | Lower pressure |
| LDHA | 0.13 ± 0.037 | 0.68 | Lower pressure |
| LDHB | 0.22 ± 0.067 | 1.11 | No phenotype |
| LDHC | 0.17 ± 0.046 | 0.88 | No phenotype |
| LDHD | 0.081 ± 0.036 | 0.41 | Lower pressure |

Figure 14

| Compound | Concentration | Pressure of treated control RNAi cells (kPa) | Relative pressure (1 = untreated control RNAi cells) | Pressure of treated DJ-1 RNAi cells (kPa) | Relative pressure (1 = untreated control RNAi cells) | Effect of compound on the DJ-1 pressure phenotype |
|---|---|---|---|---|---|---|
| Glucose | 20 mM | 0.17 ± 0.040 | 0.89 | 0.15 ± 0.071 | 0.81 | Rescue |
| Galactose | 20 mM | 0.17 ± 0.050 | 1.06 | 0.083 ± 0.060 | 0.52 | No rescue |
| Fructose | 20 mM | 0.23 ± 0.029 | 1.10 | 0.17 ± 0.067 | 0.81 | No rescue |
| Trehalose | 5 mM | 0.19 ± 0.040 | 1.15 | 0.11 ± 0.062 | 0.64 | No rescue |
| Maltose | 20 mM | 0.22 ± 0.054 | 1.05 | 0.12 ± 0.070 | 0.56 | No rescue |
| Sucrose | 20 mM | 0.25 ± 0.055 | 1.19 | 0.16 ± 0.058 | 0.78 | No rescue |
| 2-deoxyglucose | 20 mM | 0.12 ± 0.069 | 0.66 | 0.039 ± 0.036 | 0.22 | Toxic |
| Glucose, 6-aminonicotinamide | 20 mM, 100 µM | 0.20 ± 0.032 | 1.05 | 0.12 ± 0.043 | 0.63 | Rescue inhibited[1] |
| Methylglyoxal | 1 mM | - | - | - | - | Lethal |
| Glyoxal | 1 mM | - | - | - | - | Lethal |
| D-lactate | 1 mM | 0.16 ± 0.039 | 0.90 | 0.16 ± 0.032 | 0.91 | Rescue |
| D-lactate | 10 mM | 0.17 ± 0.056 | 0.96 | 0.16 ± 0.030 | 0.90 | Rescue |
| L-lactate | 1 mM | 0.15 ± 0.036 | 0.93 | 0.11 ± 0.038 | 0.67 | No rescue |
| L-lactate | 10 mM | 0.21 ± 0.074 | 1.62 | 0.11 ± 0.065 | 0.81 | No rescue |
| Glycolate | 1 mM | 0.16 ± 0.029 | 1.00 | 0.15 ± 0.033 | 0.93 | Rescue |
| Glycolate | 10 mM | 0.16 ± 0.042 | 1.01 | 0.16 ± 0.059 | 1.07 | Rescue |
| Pyruvate | 5 mM | 0.14 ± 0.041 | 0.86 | 0.086 ± 0.065 | 0.54 | No rescue |
| Glutamine | 10 mM | 0.14 ± 0.067 | 0.87 | 0.059 ± 0.040 | 0.37 | No rescue |
| Glyoxylate | 1 mM | 0.24 ± 0.067 | 0.95 | 0.099 ± 0.085 | 0.39 | No rescue |
| Glycine | 1 mM | 0.24 ± 0.050 | 1.32 | 0.13 ± 0.072 | 0.75 | No rescue |
| KCN | 1 mM | 0.19 ± 0.041 | 1.09 | 0.15 ± 0.041 | 0.85 | Partial rescue[2] |
| KCl | 1 mM | 0.18 ± 0.048 | 1.03 | 0.089 ± 0.044 | 0.51 | No rescue |
| Nitric oxide | 20 µM | 64 ± 10 nN | 1.00 | 42 ± 16 nN | 0.65 | No rescue[3] |
| Nitric oxide | 100 µM | 67 ± 19 nN | 1.05 | 65 ± 12 nN | 1.00 | Rescue[3] |
| Nitric oxide | 500 µM | 12 ± 11 nN | 0.19 | 14 ± 13 nN | 0.22 | Toxic[3] |
| Azide | 1 mM | 58 ± 18 nN | 1.12 | 50 ± 19 nN | 0.97 | Rescue[3] |
| Azide | 5 mM | 61 ± 16 nN | 1.18 | 65 ± 13 nN | 1.27 | Rescue[3] |
| Azide | 25 mM | - | - | - | - | Lethal |

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm918_ext_fwd"
      /organism="Artificial Sequence"

<400> SEQUENCE: 1
cgacgagttg cgtatgagaa                                              20

<210> SEQ ID NO 2
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm918_ext_rev"
      /organism="Artificial Sequence"

<400> SEQUENCE: 2
cacaagtttt tcggggagaa                                              20

<210> SEQ ID NO 3
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm918_int_fwd"
      /organism="Artificial Sequence"

<400> SEQUENCE: 3
tatgccggat tagatggagc                                              20

<210> SEQ ID NO 4
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm951_ext_fwd"
      /organism="Artificial Sequence"

<400> SEQUENCE: 4
gatttcttcg gcgtcttctg                                              20

<210> SEQ ID NO 5
<211> LENGTH: 20
<212> TYPE: DNA
<213> ORGANISM: Artificial Sequence
```

-continued

```
<220> FEATURE:
<221> NAME/KEY: source
<222> LOCATION: 1..20
<223> OTHER INFORMATION: /mol_type="unassigned DNA"
      /note="tm951_ext_rev"
      /organism="Artificial Sequence"

<400> SEQUENCE: 5
cacatctcgg gccactattt                                               20

<210> SEQ ID NO 6
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm951_int_fwd"
      /organism="Artificial Sequence"

<400> SEQUENCE: 6
aaaatgcaac gaccgacttc                                               20

<210> SEQ ID NO 7
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm1266_ext_fwd"
      /organism="Artificial Sequence"

<400> SEQUENCE: 7
tcctccgctc gcttttctc                                                20

<210> SEQ ID NO 8
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm1266_ext_rev"
      /organism="Artificial Sequence"

<400> SEQUENCE: 8
ttgcaagttg cttcgcatcc                                               20

<210> SEQ ID NO 9
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="tm1266_int_fwd"
      /organism="Artificial Sequence"

<400> SEQUENCE: 9
tcgaagcttt ggtcgtttcg                                               20
```

GLYCOLIC ACID AND/OR D-LACTIC ACID FOR THE TREATMENT OF NEURODEGENERATIVE DISEASES

CROSS-REFERENCES TO RELATED APPLICATIONS

This application is the U.S. National Stage of International Application No. PCT/EP2015/057023, filed Mar. 31, 2015, which designated the United States and has been published as International Publication No. WO 2015/150383 and which claims the priority of European Patent Application, Serial No. 14162874.3, filed Mar. 31, 2014, pursuant to 35 U.S.C. 119 (a)-(d).

BACKGROUND OF THE INVENTION

The present invention relates to glycolic acid or a pharmaceutically acceptable salt or ester thereof, and/or D-lactic acid or a pharmaceutically acceptable Salt or ester thereof for use in the treatment of a neurodegenerative disease which is associated with a decline in mitochondrial activity. The present invention also relates to a pharmaceutical formulation comprising glycolic acid or a pharmaceutically acceptable salt or ester thereof in an amount of at least 0.005% (w/w), preferably at least 0.0075% (w/w) and most preferably at least 0.01% (w/w), and/or D-lactic acid or a pharmaceutically acceptable salt or ester thereof in an amount of at least 1.5% (w/w), preferably at least 3% (w/w) and most preferably at least 4.5% (w/w).

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The term "neurodegenerative diseases" Is an umbrella term for diseases being associated with progressive loss of structure or function of neurons, including cell death of neurons. There are many parallels between different neurodegenerative disorders including atypical protein assemblies as well as induced cell death (in particular apoptosis). Neurodegenerative diseases affect many body activities, such as balance, movement, talking, breathing, and heart function. Many of these diseases are genetic. Sometimes the cause is a medical condition such as alcoholism, a tumor, or a stroke. Other causes may include toxins, chemicals, and viruses. The cause of some is, however, still not known.

One example of a neurodegenerative disease is Parkinson's disease. Parkinson's disease is caused by inexorable deterioration of dopaminergic neurons from the substantia nigra. Although little is known about the onset of Parkinson's disease, one clue is that a number of genes associated with the onset of Parkinson's disease are linked with mitochondrial activity (Corti et al., 2011). There is strong evidence that mitochondrial dysfunction and oxidative stress play a causal role in Parkinson's disease and in neurodegenerative disease pathogenesis in general. Other neurodegenerative diseases in which mitochondrial dysfunction and oxidative stress were observed include but are not limited to Alzheimer's disease, Huntington's disease, and amyotrophic lateral sclerosis (ALS) (Lin and Beal (2006), Nature 443, 787-795).

Neurodegenerative diseases are among the most serious health problems facing modern society. Many of these disorders become more common with advancing age, including Alzheimer's disease, Parkinson's disease, amyotrophic lateral sclerosis, and many others. The burden of these neurodegenerative diseases is growing inexorably as the population ages, with enormous economic and human costs. For example, Alzheimer's Disease International (ADI) estimates in its 2010 report that there are 35.6 million people with AD worldwide as of 2010, and that this will grow to 115.4 million people by 2050. In industrialized countries the prevalence of Parkinson's disease is about 1% for people over 60, with estimates of up to 4% for people in the highest age groups (Lau and Breteler (2006), Lancet Neurol.; 5(6):525-35).

To date a combination of vitamins, optimize patients' nutrition and general health, and prevent worsening of symptoms during times of illness and physiologic stress is used to treat neurodegenerative diseases (see Parikh et al (2009), Current Treatment Options in Neurology, 11:414-430 for review). However, most neurodegenerative diseases have no cure or a can only be insufficiently cured. Hence, there is an ongoing need of novel treatment possibilities that may help improving symptoms, relieve pain, and increase mobility in patients suffering from a neurodegenerative disease.

SUMMARY OF THE INVENTION

The present invention relates in a first embodiment to glycolic acid or a pharmaceutically acceptable salt or ester thereof, and/or D-lactic acid or a pharmaceutically acceptable salt or ester thereof for use in the treatment of a neurodegenerative disease which is associated with a decline in mitochondrial activity.

Also described herein is a corresponding method of treatment of a neurodegenerative disease which is associated with a decline in mitochondrial activity, said method comprising the administration of an effective amount of glycolic acid or a pharmaceutically acceptable salt or ester thereof, and/or an effective amount of D-lactic acid or a pharmaceutically acceptable salt or ester thereof to a subject having a neurodegenerative disease which is associated with a decline in mitochondrial activity.

Glycolic acid (GA) has the IUPAC name 2-hydroxyethanoic acid and the molecular formula $C_2H_4O_3$. Glycolic acid is used in the prior art, for example, in the textile industry as a dyeing and tanning agent, in food processing as a flavouring agent and as a preservative, and in the pharmaceutical industry as a skin care agent. Glycolic acid can also be found in sugar beets, Sugarcane and various fruits. Traces of glycolic acid are present, for example, in unripe or green grapes. Glycolic acid is also found in pineapple and cantaloupe.

Lactic acid has the IUPAC name 2-hydroxypropanoic acid and the molecular formula $C_3H_8O_3$. Lactic acid is found primarily in sour milk products, such as koumiss, laban, yogurt, buttermilk, kefir, Some Cottage cheeses and kombucham but also, for example, in pickled vegetables, and cured meats and fish. As a food additive it is, for example, approved for use in the EU, US, Australia, and New Zealand. Lactic acid is furthermore listed by its INS number 270 or as E number E270. Lactic acid is used in the art as a food preservative, curing agent, and flavoring agent. It is an ingredient in processed foods and is used as a decontaminant during meat processing.

Lactic acid is chiral and has two optical isomers. One isomer is L-(+)-lactic acid (LL) or (S)-lactic acid, and its mirror image, the other isomer, is D-(−)-lactic acid (DL) or (R)-lactic acid. D- and L-lactic acid are produced naturally by lactic acid bacteria. High level of D-lactic acid is found in many fermented milk products such as yoghurt and cheese. In accordance with the present invention D-lactic acid is used as active ingredient for the treatment of a neurodegenerative disease which is associated with a decline in mitochondrial activity. As can be taken from the examples herein below, L-lactic acid is surprisingly not suitable to treat a neurodegenerative disease which is associated with a decline in mitochondrial activity.

A pharmaceutically acceptable salt of glycolic acid includes but is not limited to sodium glycolate, potassium glycolate, calcium glycolate, magnesium glycolate, barium glycolate, aluminium gylcolate, hydrochloride, hydrobromide, Oxalate, nitrate, sulphate, phosphate, fumarate, Succinate, maleate, besylate, tosylate, tartrate, and palmitate. Likewise a pharmaceutically acceptable salt of lactic acid includes but is not limited to sodium lactate, potassium lactate, calcium lactate, magnesium lactate, barium lactate, and aluminium lactate, hydrochloride, hydrobromide, oxalate, nitrate, sulphate, phosphate, succinate, maleate, fumarate, besylate, tosylate, tartrate, and palmitate.

A pharmaceutically acceptable ester of glycolic acid includes but is not limited to methyl glycolate, and ethyl glycolate. Likewise a pharmaceutically acceptable ester of lactic acid includes but is not limited to methylactate and ethylactate.

In cases were both GA and/DL are used for the treatment they may either be administered at the same time, or may be administered one after another, wherein in the latter case the time preferably is selected such that GA and DL can act together in the treatment of a neurodegenerative disease being associated with a mitochondrial decline. In cases where the GA and DL are administered at the same time GA and DL may either be co-formulated before administration or separately administered.

The term "treatment" as used herein comprises a (partially or fully) curative treatment and in particular encompasses the stop or the deferral of the progression of the disease to be treated.

A neurodegenerative disease is defined as a hereditary or Sporadic Condition which are both characterized by progressive nervous system dysfunction. A neurodegenerative disease thus results in progressive degeneration and/or death of nerve cells. These disorders are often associated with atrophy of the affected central or peripheral structures of the nervous system. In all major examples of neurodegenerative diseases there is strong evidence that mitochondrial dysfunction occurs early and acts causally in disease pathogenesis (Lin and Beal (2006), Nature 443, 787-795).

The most common form of neuronal cell death in neurodegeneration is the intrinsic mitochondrial apoptotic pathway. This pathway Controls the activation of caspase-9 by regulating the release of cytochrome c from the mitochondrial intermembrane space (IMS). Reactive oxygen species (ROS) are normal byproducts of mitochondrial respiratory chain activity. ROS concentration is mediated by mitochondrial antioxidants such as manganese superoxide dismutase (SOD2) and glutathione peroxidase. Over production of ROS (oxidative stress) is a central feature of all neurodegenerative disorders. In addition to the generation of ROS, mitochondria are also involved with life-sustaining functions including calcium homeostasis, PCD, mitochondrial fission and fusion, lipid concentration of the mitochondrial membranes, and the mitochondrial permeability transition. Mitochondrial disease leading to neurodegeneration is believed, at least on some level, to involve all of these functions (DiMauro and Schon (2008), Annual Review of Neuroscience 31: 91-123)

Initial experimental results made in connection with this invention were obtained with HeLa cells, wherein the DJ-1 gene (also known as Parkinson disease (autosomal recessive, early onset) 7, or PARK7) was knocked-down by RNAI. DJ-1 was first discovered as an oncogene (Nagakubo et al., 1997) and is associated with familial forms of Parkinson's disease, which is a slow progressive neurodegenerative disease characterized by the loss of dopaminergic neurons in the substantia nigra (Goedert et al., 2013; Bonifati et al., 2003). It was found that RNAI in HeLa cells did not produce an altered mitochondrial phenotype (FIG. 2B).

It was then unexpectedly found that the addition of low doses of paraquat, an environmental poison known to affect mitochondria (Sal et al., 2012), and implicated in the onset of Parkinson's disease, disrupted mitochondrial structure in DJ-1 RNAI cells (FIG. 2B). Mitochondria took on a more circular structure. A circular mitochondrial phenotype is a common indicator of mitochondrial stress (Kanazawa et al., 2008). This circular phenotype was surprisingly rescued by the addition of DL or GA (FIG. 2B, C, FIG. 9). By contrast, this circular phenotype was not rescued by the addition of any of the other tested metabolites, namely glucose, pyruvate and glutamine.

Based upon the finding that GA and DL can rescue the cell rounding phenotype of DJ-1 mutations it was investigated whether DL and GA can stimulate the survival of dopaminergic neurons in vitro (FIG. 4A) and in vivo within dopaminergic neurons. This led to the key finding of the present invention, namely that GA and DL stimulate the survival of dopaminergic neurons in vitro (FIG. 4A) and in vivo within dopaminergic neurons from DJ-1 knock out mice (FIG. 12). Furthermore, it was found that GA and DL significantly rescue the toxic effect of paraquat on neurons (FIG. 4B). These results evidence an important role of GA and DL in survival of dopaminergic neurons. The further data discussed in the examples herein below Indicates that the enhanced survival by GA and DL in some way involves maintaining mitochondrial potential, which in turn is related to the network structure of mitochondria. GA and DL are believed to act via a role in signaling, or as cofactors in the activity of enzymes or structural proteins necessary for mitochondrial function.

The discovery of the invention that GA and DL can protect neurons, consequently implies a therapeutic use of GA and/or DL for the treatment of neurodegenerative diseases which are associated with a decline in mitochondrial activity that includes preventive strategies. Providing neurons of a patient (preferably a human) having a neurodegenerative disease which is associated with a decline in mitochondrial activity with these substances is expected to protect the neurons of the patient against metabolic or environmental stress. Noteworthy many diseases are associated with a decline in mitochondrial activity (Schapira, 2012), thereby underlining the importance of the finding of the present invention. Also noteworthy neurodegenerative diseases are characterized by Cell death of neurons. Hence, it has been found in connection with the invention that DL and GA—both enhancing the survival of neurons—have a direct effect against a mechanism being specifically involved in the progression of neurodegenerative diseases. This inevitably evidences the suitability of DL and GA for the treatment of neurodegenerative diseases which is associated with a decline in mitochondrial activity in accordance with the first embodiment of the present invention.

In a preferred embodiment of the invention, the disease being associated with a decline in mitochondrial activity is selected from the group consisting of Parkinson's disease, Alzheimer's disease, Huntington's disease, Amyotrophic lateral sclerosis, and other neurodegenerative diseases.

Parkinson's disease (PD) belongs to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and Coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes, difficulty in swallowing, chewing, and speaking; urinary problems or constipation; skin problems; and sleep disruptions. There are currently no blood or laboratory tests that have been proven to help in diagnosing sporadic PD. Therefore the diagnosis is based on medical history and a neurological examination. The disease can be difficult to diagnose accurately. Doctors may sometimes request brain scans or laboratory tests in order to rule out other diseases (see http://www.ninds.nih.gov/disorders/parkinsons_disease/parkinsons_disease.htm).

Alzheimer's disease (AD) is an age-related, non-reversible brain disorder that develops over a period of years. Initially, people experience memory loss and confusion, which may be mistaken for the kinds of memory changes that are sometimes associated with normal aging. However, the symptoms of AD gradually lead to behavior and personality changes, a decline in cognitive abilities such as decision-making and language skills, and problems recognizing family and friends. AD ultimately leads to a severe loss of mental function. These losses are related to the worsening breakdown of the connections between certain neurons in the brain and their eventual death. AD is one of a group of disorders called dementias that are characterized by cognitive and behavioral problems. It is the most Common cause of dementia among people age 65 and older. There are three major hallmarks in the brain that are associated with the disease processes of AD. (i) Amyloid plaques, which are made up of fragments of a protein called beta-amyloid peptide mixed with a collection of additional proteins, remnants of neurons, and bits and pieces of other nerve cells. (ii) Neurofibrillary tangles (NFTs), found inside neurons, are abnormal collections of a protein called tau. Normal tau is required for healthy neurons. However, in AD, tau clumps together. As a result, neurons fail to function normally and eventually die. (iii) Loss of connections between neurons responsible for memory and learning. Neurons cannot survive when they lose their connections to other neurons. As neurons die throughout the brain, the affected regions begin to atrophy, or shrink. By the final stage of AD, damage is widespread and brain tissue has shrunk significantly (see http://www.ninds.nih.gov/disordersfalzhemersdiseasefalzhelmersdisease.htm).

Huntington's disease (HD) results from genetically programmed degeneration of brain cells, called neurons, in certain areas of the brain. This degeneration causes uncontrolled movements, loss of intellectual faculties, and emotional disturbance. HD is a familial disease, passed from parent to child through a mutation in the normal gene. Each child of an HD parent has a 50-50 chance of inheriting the HD gene. If a child does not inherit the HD gene, he or she will not develop the disease and cannot pass it to subsequent generations. A person who inherits the HD gene will sooner or later develop the disease. Whether one child inherits the gene has no bearing on whether others will or will not inherit the gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person. A genetic test, coupled with a complete medical history and neurological and laboratory tests, helps physicians diagnose HD. Presymptomic testing is available for individuals who are at risk for carrying the HD gene. In 1 to 3 percent of individuals with HD, no family history of HD can be found (see http://www.ninds.nih.gov/disorders/huntington/huntington.htm).

Amyotrophic lateral sclerosis (ALS), sometimes called Lou Gehrig's disease or classical motor neuron disease, is a rapidly progressive, invariably fatal neurological disease that attacks the nerve cells (neurons) responsible for controlling Voluntary muscles. In ALS, both the upper motor neurons and the lower motor neurons degenerate or die, ceasing to send messages to muscles. Unable to function, the muscles gradually Weaken, waste away, and twitch. Eventually the ability of the brain to start and control voluntary movement is lost. Symptoms are usually first noticed in the arms and hands, legs, or Swallowing muscles. Muscle weakness and atrophy occur on both sides of the body. Individuals with ALS lose their strength and the ability to move their arms and legs, and to hold the body upright. When muscles in the diaphragm and chest wall fail to function properly, individuals lose the ability to breathe without ventilatory support. The disease does not affect a person's ability to see, smell, taste, hear, or recognize touch. Although the disease does not usually impair a person's mind or personality, several recent studies suggest that some people with ALS may develop cognitive problems involving word fluency, decision-making, and memory. The cause of ALS is not known, and scientists do not yet know why ALS strikes some people and not others (see http://www.ninds.nih.gov/disorderSlamyotrophiclateralsclerosis/ALS.htm).

All mentioned neurodegenerative diseases, i.e. Parkinson's disease, Alzheimer's disease, Huntington's disease, amyotrophic lateral Sclerosis are known to be associated with a decline in mitochondrial activity (Lin and Beal (2006), Nature 443, 787-795). Means and methods for determining the mitochondrial activity are known in the art, for example from Agnello et al. (2008), Cytotechnology, 56(3):145-149.

In accordance with a more preferred embodiment of the invention, the disease being associated with a decline in mitochondrial activity is Parkinson's disease.

As discussed above, n the examples herein below HeLa cells having knocked down the Parkinson's disease-related gene DJ-1 are used as model for Parkinson's disease. Hence, the examples herein below provide evidence that glycolic acid and/or D-lactic acid are suitable for the treatment of Parkinson's disease.

Therapeutic routes for Parkinson's disease have so far been intractable. It has been shown that environmental toxins that affect mitochondria are strongly linked to the appearance of Parkinson's disease (Freire and Kolfman, 2012; Song et al., 2004) and impairment of the mitochondrial function is a common feature of both idiopathic and genetic Parkinson's disease (Burchell et al., 2013; Wang et al., 2012; Kamp et al, 2010 Irrcher et al, 2010 Clark et al., 2006, Park et al., 2006, Schapira et al., 1989). Recent studies suggest that the interaction between alpha-synuclein oligomers and mitochondria could be an underlying mechanism by which Parkinson's progresses (Braidy et al., 2013; Pan-Montojo et al., 2012). The discovery of the invention that the production of molecules from endogenous enzymatic pathways, namely D-lactic acid and glycolic acid can protect neurons, offers a novel therapeutic direction that is expected to include preventive strategies. Both products of glyoxalases exist in many natural products. Thus, providing neurons with these substances has an enormous potential to protect neurons against metabolic or environmental stress. Because many diseases are associated with a decline in mitochondrial activity (Schapira, 2012), the products of glyoxalases we expect to have a general role in protecting cells from decline.

In another preferred embodiment of the invention, the glycolic acid or a pharmaceutically acceptable salt or ester thereof, and/or the D-lactic acid or a pharmaceutically acceptable salt or ester thereof are comprised in a formulation, said formulation containing (i) at least 0.005% (w/w), preferably at least 0.0075% (w/w) and most preferably at least 0.010% (w/w) of glycolic acid and a pharmaceutically acceptable salt or ester thereof, and/or (ii) at least 1.0% (w/w), preferably at least 1.5% (w/w), more preferably at least 3% (w/w) and most preferably at least 4.5% (w/w) of D-lactic acid or a pharmaceutically acceptable salt or ester thereof.

The skilled person can determine a suitable daily dose of such formulations as well as a suitable daily dosage in case glycolic acid or a pharmaceutically acceptable salt or ester thereof, and/or the D-lactic acid or a pharmaceutically acceptable salt or ester thereof are directly administered to a subject. The administered amounts of glycolic acid or a pharmaceutically acceptable salt or ester thereof, and/or the D-lactic acid or a pharmaceutically acceptable salt or ester thereof on the one hand have to be sufficient for the treatment of a neurodegenerative disease which is associated with a decline in mitochondrial activity, and on the other hand should not be so high as to generate an acidosis in the subject to be treated. Acidosis is an increased acidity in the blood and other body tissue. Acidosis is said to occur when the blood, serum or body tissue pH falls below 7.35. Means and methods to determine the pH in blood, serum and body tissue are well-known.

The toxic effect of too much glycolic acid is known, for example, from the 1985 diethylene glycol wine scandal. The scandal involved a limited number of Austrian wineries that had illegally adulterated their wines using the toxic Substance diethylene glycol (a primary Ingredient in some brands of antifreeze) to make the wines appear Sweeter and more full bodied. The major cause of toxicity is not the ethylene glycol itself but its major metabolite glycolic acid. The minimum toxic dose of diethylene glycol is estimated at 0.14 mg glycolic acid per kg of body weight and the lethal dose is estimated between 1.0 and 1.63 g/kg. Hence, the preferred dose of glycolic acid and a pharmaceutically acceptable salt or ester thereof is selected such that total glycolate levels do not exceed 0.14 mg glycolate per kg of body weight. Preferred lower amounts to be combined with the maximum amount are with increasing preference 0.01, 0.03, 0.05, 0.075 and 0.1 mg glycolate per kg of body weight.

Lactic acidosis is a physiological condition characterized by low pH in body tissues and blood (acidosis) accompanied by the buildup of lactate, and is considered a distinct form of metabolic acidosis. Lactic acidosis is characterized by lactate levels >5 mmol/L and blood, serum and body tissue pH below 7.35. The lactate concentration in plasma is normally 0.4 to 1.0 mmol/L. Hence, the preferred dose of D-lactic acid and a pharmaceutically acceptable salt or ester thereof is selected such that the total lactate levels in blood, serum and body tissue are in the range of 1.0 mmol/L to 5.0 mmol/L.

A formulation prepared in accordance with the invention comprises at least two components in an appropriate relationships two each other, wherein at least one of the two components is glycolic acid or a pharmaceutically acceptable salt or ester thereof, or D-lactic acid or a pharmaceutically acceptable salt or ester thereof. The second of the at least two components of a formula may be a simple carrier, for example water. A formulation may be a mixture or a structure such as a liquid, a capsule, a pill, a tablet, or an emulsion, prepared according to a specific procedure (called a "formula"). Formulations are a very Important aspect of creating drugs. Formulas may ensure, for example, that the active ingredient of a drug—being in the present invention glycolic acid or a pharmaceutically acceptable Salt or ester thereof, and/or D-lactic acid or a pharmaceutically acceptable or ester salt thereof—is delivered to the correct part of the body, in the right concentration, and/or at the right release rate (not too fast and not too slowly). In accordance with the invention one component of the formula has to be (i) glycolic acid or a pharmaceutically acceptable salt or ester thereof, or (ii) D-lactic acid or a pharmaceutically acceptable salt or ester thereof.

Glycolic acid (GA) is naturally present in a variety of fruits, vegetables, meats and beverages, however in amount being lower as 50 mg/kg (see Harris and Richardson (1980), Investigative Urology, 18:106-109). 50 mg/kg correspond to 0.005% (w/w). Hence, the formulation of the invention comprises more glycolic acid and a pharmaceutically acceptable salt or ester thereof than the amount of glycolic acid found in natural food.

Also D-lactic acid is present in natural food. The amount of lactic acid (both L- and D-lactic acid) in food products is defined according to Good Manufacturing Practice (GMP). The regular amount of lactic acid is, for example, for yoghurt about 0.8% (w/w), and for buttermilk 1.5% (w/w). In a toxicology study, even about 8 g/day of lactic acid have been declared as harmless. In buttermilk the majority of lactic acid is L-lactic acid. However, in case yoghurt is made by Bulgarian strains of *Lactobacillus bulgaricus/acidophilus* about 90% of the lactic acid is D-lactic acid. Hence, the formulation of the invention comprises more D-lactic acid or a pharmaceutically acceptable salt or ester thereof than the amount of D-lactic acid found in natural food.

In a further preferred embodiment of the invention, in addition pyruvate is used for the treatment of said disease which is associated with a decline in mitochondrial activity.

A formulation in accordance with this preferred embodiment may comprise with increasing preference at least 1.0% (W/w), at least 1.5% (w/w), preferably at least 3% (w/w) and at least 4.5% (w/w) of D-lactic acid or a pharmaceutically acceptable salt or ester thereof and in addition pyruvate. Likewise a formulation in accordance with this preferred embodiment may comprise with increasing preference at least 0.005% (w/w), at least 0.0075% (w/w) and at least 0.01% (w/w) of glycolic acid and a pharmaceutically acceptable salt or ester thereof and in addition pyruvate. In addition, a formulation in accordance with this preferred embodiment may comprise with increasing preference at least 1.0% (w/w), and at least 1.5% (w/w), preferably at least 3% (w/w) and at least 4.5% (w/w) of D-lactic acid or a pharmaceutically acceptable salt or ester thereof, with increasing preference at least 0.005% (w/w), at least 0.0075% (w/w) and at least 0.01% (w/w) of glycolic acid and a pharmaceutically acceptable salt or ester thereof and in addition pyruvate.

Pyruvate has the molecular formula $CH_3COCOO^-$ and the IUPAC name 2-oxopropanoic acid salt. Pyruvate supplies energy to living cells through the citric acid cycle (also known as the Krebs cycle) when oxygen is present (aerobic respiration), and alternatively ferments to produce lactic acid when oxygen is lacking (fermentation). Tanaka et al. (2007), Mitochondrion, 7(6):399-401, for example, describes the therapeutic potential of pyruvate therapy for mitochondrial diseases. Since it has been found in Connection with the present invention that pyruvate cannot rescue the circular phenotype of DJ-1 depleted cells, pyruvate acts by a different mechanism as glycolic acid and D-lactic acid. Hence, combining pyruvate with D-lactic acid or a pharmaceutically acceptable salt or ester thereof, and/or glycolic acid and a pharmaceutically acceptable salt or ester thereof can be expected to have an additive beneficial or even synergistic effect in the treatment of a neurodegenerative disease which is associated with a decline in mitochondrial activity.

In a still further preferred embodiment of the invention, in addition one or more antioxidants, preferably comprising coenzyme Q10 is/are used for the treatment of said disease which is associated with a decline in mitochondrial activity.

A formulation in accordance with this preferred embodiment may comprise with increasing preference at least 1.0% (w/w), at least 1.5% (w/w), preferably at least 3% (w/w) and at least 4.5% (w/w) of D-lactic acid or a pharmaceutically acceptable salt or ester thereof and in addition one or more antioxidants, preferably comprising Coenzyme Q10, and optionally pyruvate. Likewise a formulation in accordance with this preferred embodiment may comprise with increasing preference at least 0.005% (w/w), at least 0.0075% (w/w) and at least 0.01% (w/w) of glycolic acid and a pharmaceutically acceptable salt or ester thereof and in addition one or more antioxidants, preferably comprising Coenzyme Q10, and optionally pyruvate. In addition, a formulation in accordance with this preferred embodiment may comprise with increasing preference at least 1.0% (w/w), at least 1.5% (w/w), preferably at least 3% (w/w) and at least 4.5% (w/w) of D-lactic acid or a pharmaceutically acceptable salt or ester thereof, and with increasing preference at least 0.005% (w/w), at least 0.0075% (w/w) and at least 0.01% (w/w) of glycolic acid and a pharmaceutically acceptable salt or ester thereof and in addition one or more antioxidants, preferably comprising Coenzyme Q10, and optionally pyruvate.

Elisa et al (2010), Muscle & Nerve, 42(5):739-748 report on a randomized trial using coenzyme Q10 (CoQ10) for the treatment of mitochondrial diseases. Case reports and open label studies suggest that coenzyme Q10 treatment appears to have beneficial effects in mitochondrial disease patients. Also Parikh et al. (2009), Current Treatment Options in Neurology, 11:414-430 suggest using coenzyme Q10 for the treatment of mitochondrial diseases. Hence, combining one or more antioxidants, in particular coenzyme Q10 with D-lactic acid or a pharmaceutically acceptable salt or ester thereof, and/or glycolic acid and a pharmaceutically acceptable salt or ester thereof can be expected to have an additive beneficial or even synergistic effect in the treatment of a neurodegenerative disease which is associated with a decline in mitochondrial activity.

CoQ10 is endogenously synthesized in mammalian mitochondria and Is an integral component of the mitochondrial electron transport chain, shuttling electrons from complexes I or II and a number of other electron donors, including electron transfer factor, which moves electrons from fatty acid beta oxidation. CoQ10 is found in all cell and organelle membranes, where it can participate in redox shuttling. It has an important intracellular signaling role, as well as both antioxidant and pro-oxidant roles. CoQ10 modulates the mitochondrial permeability transition pore involved in apoptosis and activates uncoupling proteins. It is known that CoQ10 biosynthetic defects underlie several different phenotypes of human mitochondrial disease (see Parikh et al. (2009), Current Treatment Options in Neurology, 11:414-430).

According to another preferred embodiment of the invention, in addition one or more vitamins, being preferably selected from Vitamin E, C, B2 and B9, is/are used for the treatment of said disease which is associated with a decline in mitochondrial activity.

A formulation in accordance with this preferred embodiment may comprise with increasing preference at least 1.0% (w/w), at least 1.5% (W/w), preferably at least 3% (w/w) and at least 4.5% (w/w) of D-lactic acid or a pharmaceutically acceptable salt or ester thereof and in addition one or more vitamins, being preferably selected from Vitamin E, C, B2 and B9, and optionally pyruvate and/or one or more antioxidants. Likewise a formulation in accordance with this preferred embodiment may comprise with increasing preference at least 0.005% (w/w), at least 0.0075% (w/w) and at least 0.001% (w/w) of glycolic acid and a pharmaceutically acceptable salt or ester thereof and in addition one or more vitamins, being preferably selected from Vitamin E, C, B2 and B9, and optionally pyruvate and/or one or more antioxidants. In addition, a formulation in accordance with this preferred embodiment may comprise with increasing preference at least 1.0% (W/w), at least 1.5% (w/w), preferably at least 3% (w/w) and at least 4.5% (w/w) of D-lactic acid or a pharmaceutically acceptable salt or ester thereof, and with increasing preference at least 0.005% (w/w), at least 0.0075% (w/w) and at least 0.01% (w/w) of glycolic acid and a pharmaceutically acceptable salt or ester thereof and in addition one or more vitamins, being preferably selected from Vitamin E, C, B2 and B9, and optionally pyruvate and/or one or more antioxidants.

As described in Parikh et al. (2009), Current Treatment Options in Neurology, 11:414-430 a combination of vitamins is presently used for the treatment of most patients suffering from a mitochondrial disease. Hence, combining vitamins with D-lactic acid or a pharmaceutically acceptable salt or ester thereof, and/or glycolic acid and a pharmaceutically acceptable salt or ester thereof can be expected to have an additive beneficial or even synergistic effect in the treatment of a neurodegenerative disease which is associated with a decline in mitochondrial activity.

Vitamin E (tocopherol) and vitamin C (ascorbic acid) are antioxidants and are therefore used in the art in the therapy of mitochondrial diseases. In more detail, accumulation of free radicals may be especially harmful to mitochondrial disease patients. The use of antioxidants, like Vitamin C and Vitamin E can help to reduce free radical accumulation, which at least in some patients may mean improvements in energy and function (see Parikh et al. (2009), Current Treatment Options in Neurology, 11:414-430).

B vitamin 2 (B2, Riboflavin) is a water-soluble vitamin that serves as a flavoprotein precursor. It is a key building block in complex I and II and a cofactor in several other key enzymatic reactions involving fatty acid oxidation and the Krebs cycle. Several non-randomized studies have shown vitamin B2 to be efficacious in treating mitochondrial diseases, in particular complex I and/or complex I disease (see Parikh et al. (2009), Current Treatment Options in Neurology, 11:414-430).

B vitamin 2 (B2, Folinic acid) is a water-soluble vitamin involved as a cofactor in multiple metabolic reactions. A few case reports and one Small case series have suggested that mitochondrial disease may lead to secondary cerebral B2 deficiency, defined by low cerebrospinal fluid (CSF) folate, especially of the C1 donor, 5-MTHF. The mechanism of cerebral B2 deficiency in mitochondrial disease is unclear; it is postulated to result from a failure to produce adequate ATP for active folate transport across the blood-brain barrier (see Parikh et al. (2009), Current Treatment Options in Neurology, 11:414-430).

In a preferred embodiment of the invention, in addition one or more of L-arginine, L-carnitine and L-creatine is/are used for the treatment of Said disease which is associated with a decline in mitochondrial activity.

A formulation in accordance with this preferred embodiment may comprise with increasing preference at least 1.0% (w/w), at least 1.5% (w/w), preferably at least 3% (w/w) and at least 4.5% (w/w) of D-lactic acid or a pharmaceutically acceptable salt or ester thereof and in addition one or more of L-arginine, L-carnitine and L-creatine, and optionally one or more of pyruvate, one or more antioxidants and one or more vitamins. Likewise a formulation in accordance with this preferred embodiment may comprise with increasing preference at least 0.005% (w/w), at least 0.0075% (w/w) and at least 0.01% (w/w) of glycolic acid and a pharmaceutically acceptable salt or ester thereof and in addition one or more of L-arginine, L-carnitine and L-creatine, and optionally one or more of pyruvate, one or more antioxidants and one or more vitamins. In addition, a formulation in accordance with this preferred embodiment may comprise with increasing preference at least 1.0% (w/w), at least 1.5% (w/w), preferably at least 3% (w/w) and at least 4.5% (w/w) of D-lactic acid or a pharmaceutically acceptable salt or ester thereof, and with increasing preference at least 0.005% (w/w), at least 0.0075% (w/w) and at least 0.01% (w/w) of glycolic acid and a pharmaceutically acceptable salt or ester thereof and in addition one or more of L-arginine, L-carnitine and L-creatine, and optionally one or more of pyruvate, one or more antioxidants and one or more vitamins.

L-arginine, L-carnitine and L-creatine are currently used for the treatment of mitochondrial diseases; see for review Parikh et al. (2009), Current Treatment Options in Neurology, 11:414-430. Hence, combining L-arginine, L-carnitine and/or L-creatine with D-lactic acid or a pharmaceutically acceptable salt or ester thereof, and/or glycolic acid and a pharmaceutically acceptable salt or ester thereof can be expected to have an additive beneficial or even synergistic effect in the treatment of a neurodegenerative disease which is associated with a decline in mitochondrial activity.

Arginine is a semi-essential amino acid involved in growth, urea detoxification, and creatine synthesis. L-arginine produces nitric oxide, which has neurotransmitter and vasodilatory properties (see Parikh et al. (2009), Current Treatment Options in Neurology, 11:414-430).

L-carnitine is a cellular compound that plays a critical role in the process of mitochondrial β-oxidation of fatty acids and the esterification of free fatty acids that may otherwise be sequestered by CoA. Carnitine transfers long-chain fatty acids across the mitochondrial inner membrane as acylcarnitine esters. These esters are oxidized to acetyl CoA, which enters the Krebs cycle and results in subsequent generation of ATP via oxidative phosphorylation (see Parikh et al. (2009), Current Treatment Options in Neurology, 11:414-430).

Creatine, a compound present in cells, combines with phosphate in the mitochondria to form phosphocreatine. It serves as a source of high-energy phosphate, released during anaerobic metabolism. It also acts as an Intracellular buffer for ATP and as an energy shuttle for the movement of high-energy phosphates from mitochondrial sites of production to cytoplasmic sites of utilization. The highest concentrations of Creatine are found in tissues with high energy demands, such as skeletal muscle and brain. Creatine is continuously replaced through a combination of diet and endogenous synthesis (see Parikh et al. (2009), Current Treatment Options in Neurology, 11:414-430).

The forgoing preferred embodiments of the invention refer to various additional components which may be used for the treatment of said disease which is associated with a decline in mitochondrial activity. It has to be understood that these additional components may also be used in accordance with the present invention in any combination. In more detail, pyruvate, one or more antioxidants, one or more vitamins, L-arginine, L-carnitine, and L-creatine may be used in any combination with GA and/or DL. The combination may comprise with increasing preference at least two, at least there, at least four and at least five compounds selected from pyruvate, one or more antioxidants, one or more vitamins, L-arginine, L-carnitine, and L-creatine. The one or more antioxidants preferably comprise coenzyme Q10, and/or the one or more vitamins is/are preferably selected from Vitamin E, C, B2 and B9. As also defined herein above, such combination formulation Comprises with increasing preference at least 1.0% (w/w), at least 1.5% (w/w), preferably at least 3% (w/w) and at least 4.5% (w/w) of D-lactic acid or a pharmaceutically acceptable salt or ester thereof. As likewise defined herein above, such combination formulation comprises with increasing preference at least 0.005% (w/w), at least 0.0075% (w/w) and at least 0.01% (w/w) of glycolic acid and a pharmaceutically acceptable salt or ester thereof.

Also in accordance with the forgoing preferred embodiments one or more compounds selected from pyruvate, one or more antioxidants, one or more vitamins, L-arginine, L-carnitine, and L-creatine may either be administered at the same time as GA and/or DL, or may be administered before or after GA and/or DL, provided in the latter case that GA and/or DL on the one hand and the selected compound(s) on the other hand still exert their activity in the body in the treatment of a neurodegenerative disease being associated with a mitochondrial decline. In cases where the GA and/or DL, and the selected compound(s) are administered at the same time the compounds may either be co-formulated before administration or separately administered.

In a preferred embodiment of the invention, the glycolic acid or a pharmaceutically acceptable salt or ester thereof, and/or D-lactic acid or a pharmaceutically acceptable salt or ester thereof is formulated as a medical food or medical food supplement.

The medical food or medical food supplement comprises with increasing preference at least 1.0% (w/w), at least 1.5% (w/w), preferably at least 3% (w/w) and at least 4.5% (w/w) of D lactic acid or a pharmaceutically acceptable Salt or ester thereof. Likewise the medical food or medical food supplement comprises with increasing preference at least 0.005% (w/w), at least 0.0075% (w/w) and at least 0.011% (w/w) of glycolic acid and a pharmaceutically acceptable salt or ester thereof. In addition, the medical food or medical food supplement comprises with increasing preference at least 1.0% (w/w), at least 1.5% (w/w), preferably at least 3% (w/w) and at least 4.5% (w/w) of D-lactic acid or a pharmaceutically acceptable salt or ester thereof, and with increasing preference at least 0.005% (w/w), at least 0.0075% (w/w) and at least 0.01% (w/w) of glycolic acid and a pharmaceutically acceptable salt or ester thereof.

Medical foods are foods that are specially formulated and intended for the dietary management of a disease that has distinctive nutritional needs that cannot be met by normal diet alone. In the US medical foods are defined in the Food and Drug Administration's 1988 Orphan Drug Act Amendments and they subject to the general food and safety labeling requirements of the Federal Food, Drug, and Cosmetic Act. Medical foods have to be held distinct from the broader category of foods. In order to be considered a medical food the formula must, at a minimum be a food for oral ingestion or tube feeding (nasogastric tube), be intended for the dietary management of a specific medical disorder, disease or condition for which there are distinctive nutritional requirements, and be intended to be used under medical supervision. As used herein a medical food is a nutritionally Complete formula while a medical food supplement is a nutritionally incomplete formula.

In a more preferred embodiment of the invention, the medical food or medical food supplement is a milk-based medical food or medical food supplement.

As discussed herein above D-lactic acid is found in many fermented milk products. Hence, medical foods containing a substantial amount of D-lactic acid may be based on these milk products. It has to be understood that the milk-based medical food or medical food comprises in accordance with the invention additional D-lactic acid or a pharmaceutically acceptable salt or ester thereof which is not already naturally comprised in a milk product. For this purpose, the milk-based medical food or medical food supplement comprises with increasing preference at least 1.0% (w/w), at least 1.5% (w/w), preferably at least 3% (w/w) and at least 4.5% (w/w) of D-lactic acid or a pharmaceutically acceptable salt or ester thereof. These (w/w) percentages of D-lactic acid are to best knowledge of the inventors above the (w/w) percentages of D-lactic acid found in natural milk products.

The present invention relates in a second embodiment to a pharmaceutical formulation comprising glycolic acid or a pharmaceutically acceptable Salt or ester thereof in an amount of at least 0.005% (w/w), preferably at least 0.0075% (w/w) and most preferably at least 0.01% (w/w), and/or D-lactic acid or a pharmaceutically acceptable Salt or ester thereof in an amount of at least 1.5% (w/w), preferably at least 3% (w/w) and most preferably at least 4.5% (w/w).

In accordance with the present invention, the term "pharmaceutical formulation" relates to a formulation for administration to a patient, preferably a human patient. The pharmaceutical formulation of the invention may, optionally, comprise further molecules, for example compounds being capable of altering the characteristics of the compounds of the invention thereby, for example, stabilizing, modulating and/or activating their function. The formulation may be in solid or liquid form and may be, inter alia, in the form of (a) powder(s), (a) tablet(s), (a) solution(s) or (an) aerosol(s). The pharmaceutical formulation of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Formulations comprising such carriers can be formulated by well known conventional methods. These pharmaceutical formulations can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician.

The pharmaceutical formulation is preferably formulated for oral, nasal tube and/or stomach tube administration. For oral administration, the pharmaceutical formulation of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate).

For oral, nasal tube or stomach tube the pharmaceutical formulated may (also) be a liquid formulation, for example, in the form of a solution, syrup, or suspension, or can be presented as a dry product for constitution with water or other suitable vehicle before use. Such liquid formulations can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxybenzoates; sorbic acids). The liquid formulations can also contain buffer salts, flavouring, coloring and sweetening agents as deemed appropriate. Administration via a nasal tube or a stomach tube is in particular envisaged if the patient is not capable to eat and/or drink.

In a preferred embodiment of the invention, the formulation is a medical food or medical food supplement. In a more preferred embodiment of the invention, the medical food or medical food supplement is a milk-based medical food or medical food supplement.

Also the (milk-based) medical food or medical food supplement is preferably formulated for oral, nasal tube and/or stomach tube administration. Suitable formulations are further detailed herein above.

In another preferred embodiment of the invention, the formulation further comprises pyruvate, one or more antioxidants, one or more vitamins, L-arginine, L-carnitine, L-creatine or a any Combination thereof. In a more embodiment of the invention, the one or more antioxidants comprise coenzyme Q10, and/or the one or more vitamins is/are selected from Vitamin E, C, B2 and B9.

BRIEF DESCRIPTION OF THE DRAWING

The figures show

FIG. 3: Glyoxalases produce glycolate and D-lactate to rescue the cell rounding defect of DJ-1-depleted cells. (A) Selected energy metabolism pathways. Key enzymes involved in the pathways were knocked down to test their effects on mitotic rounding pressure. Substances were added to the DJ-1 RNAi cells in an attempt to rescue reduced rounding pressure. Examples of the effects are in the box. Glo-6-P, glucose-6-phosphate; Fru1,6-bisP, fructose-1,6-bisphosphate; GAP, glyceraldehyde-3-phosphate; DHAP, dihydroxyacetone phosphate; 2-DG, 2-deoxyglucose, GYS, glycogen synthase, ALDOA/B/C, aldolases, TPI1, triose phosphate isomerase; GAPDH, glyceraldehyde-3-phosphate dehydrogenase, Glo I, glyoxalase I; Glo II, glyoxalase II; LDHA/B/C, lactate dehydrogenases; LDHD, D-lactate dehydrogenase. Dashed lines show putative sources of glyoxal and methylglyoxal. Green line shows the protective effect of GA and DL on mitochondia. (B) Mean ATP levels normalized to total protein in RNAi-downregulated cells. Oligomycin A (OLA) and 2-DG were used to suppress ATP production. Error bars represent SD. n=5. (C) Rounding pressure of the DJ-1 GLO1 double RNAi-treated cells in the presence of glucose, GA, DL, and LL. Points show individual cells, horizontal blue bars and error bars represent the mean and SD, respectively. p<0.01, *p<0.001.

FIG. 5: DJ-1 is required for mitotic cell pressure generation. (A) Left, Schematic of a fast force measurement assay. Right, Example of a measurement. (B) Schematic of a rounding pressure assay. A metaphase cell was first compressed with a tipless cantilever at 14 μm, then the cantilever was lowered to 8 um at 0.1 um/sec to measure the peak ($F_{peak}$) and the equilibrium ($F_{8\ \mu m}$) rounding forces. The maximal cross section area of the compressed cell was measured to calculate cell volume and rounding pressure corresponding to Fam. Right graph, a typical measurement. Red, rounding force, blue, height of the cantilever from the substrate. (C) Rounding pressure and volume of HeLa cells RNAi knocked down of the selected Parkinson's diseases genes. Result is representative of at least three independent tests, showing data of Individual cells with the mean and standard deviation (SD). *p<0.05; p<0.01; *p<0.001. (D) Rounding pressure of metaphase HeLa cells in the trans-mitotic measurement experiment (FIG. 1B). The maximal cell pressure during metaphase is plotted, with the mean (blue) and SD. (E) Rounding pressure of HeLa cells expressing mouse DJ-1 transgene. As the esiRNA for human genes does not usually affect mouse ortholog expression (Kittler et al., 2005), the lower rounding pressure phenotype was rescued by the mouse DJ-1 transgene (fourth group). Pressure of individual mitotic cells was shown with mean (blue) and SD. A typical result of independent tests is shown. (F) Volume of mitotic mouse embryonic fibroblast (MEF). Mitotically arrested wild type (WT) and DJ-1 knock-out (KO) MEFs were compressed to measure rounding pressure (FIG. 1c) and volume. Data of the individual cells are plotted with mean and SD. Result is representative of three independent experiments. (G) Expression of DJ-1 protein in MEFs and RNAi-treated HeLa cells. DJ-1 and tubulin proteins in the lysate were detected in Immunoblotting. No DJ-1 protein detected in KO MEFs. By a densitometric analysis, RNAi of DJ-1 downregulated its expression by 75% in HeLa cells.

FIG. 11: Glyoxalases produce glycolate and D-lactate to rescue the cell rounding defect of DJ-1-depleted cells. (A) immunoblot of DJ-1 in control and DJ-1 RNAi cells. Tubulin serves as a loading control. (B) ATP:ADP ratio of the RNAI-treated HeLa cells in the presence of glucose. RNAi-treated cells were lysed in perchloric acid. Neutralized and filtered lysates were separated in reversed-phase HPLC. Relative abundance of ATP to ADP is plotted. (C) Immunoblot of DJ-1 and GLO1 in control, DJ-1- and GLO1-RNAi-treated HeLa cells. Tubulin serves as a loading control. Double RNAi of DJ-1 and GLO-1 efficiently downregulates the expression of both proteins. (D) Volume of the DJ-1 GLO1 double RNAitreated cells in the presence of glucose (Glc), GA, DL, and LL. See FIG. 3c for the corresponding cell pressure result. Result is representative of two independent experiments, showing individual cell data with mean (blue) and SD.

FIG. 12: Glycolate, D-lactate, and glucose support in vitro survival of the dopaminergic neuron. (A) Survival of the primary dopaminergic neurons in the presence of the different concentrations of D-lactate, glycolate, and glucose (Glc). The primary neurons from wild type mouse embryos were cultured with the indicated substances for 6 days, fixed, and stained for tyrosine hydroxylase (TH), a dopaminergic neuron-specific marker. The relative number of the $TH^+$ cells to none-treated control was plotted, with mean and SD. Each dot indicates an independent experiment. (B) immunoblot of DJ-1 in wild type and DJ-1 mutant mouse brain. Total brains isolated from wild type and DJ-1 mutant adults and embryos were lysed, and tested for DJ-1 expression. Tubulin is the loading control.

FIG. 13: Effect of depletion of energy metabolism genes on mitotic rounding pressure. The indicated genes were RNAi-depleted in HeLa cells, and rounding pressure of metaphase cells was measured on the AFM. Mean rounding pressure it SD was shown, as well as the relative pressure value to that of Luciferase control RNAi cells. In the rightmost column, the effect of RNAI was annotated by statistical significance to the control.

FIG. 14: Effect of the substances on the lower pressure phenotype in mitotic DJ-1 RNAi cells. Control (Luc) and DJ-1 RNAi-treated cells were treated with the indicated substances, many of which were shown in FIG. 3a. After 1 hour, pressure or rounding force of mitotic HeLa cells was measured on the AFM. Meant SD as well as the relative pressure/force value to that of untreated control was shown. In the rightmost column, the effect of the compound was annotated by statistical significance: Rescue, the substance restored pressure of DJ-1 RNAi cells to that of control RNAi cells, No rescue, the substance did not significantly change pressure of DJ-1 RNAi cells, Toxic, the substance affected cell pressure both in control and DJ-1 RNAI cells[1], the glucose-mediated rescue was inhibited by 6-aminonicotinamide, an inhibitor of the pentose-phosphate pathway[2], treatment caused rounding pressure that is higher than that of untreated DJ-1 RNAi cells but lower than that of untreated control RNAi cells.[3], rounding force was measured.

DETAILED DESCRIPTION OF PREFERRED EMBODIMENTS

Figure 1:
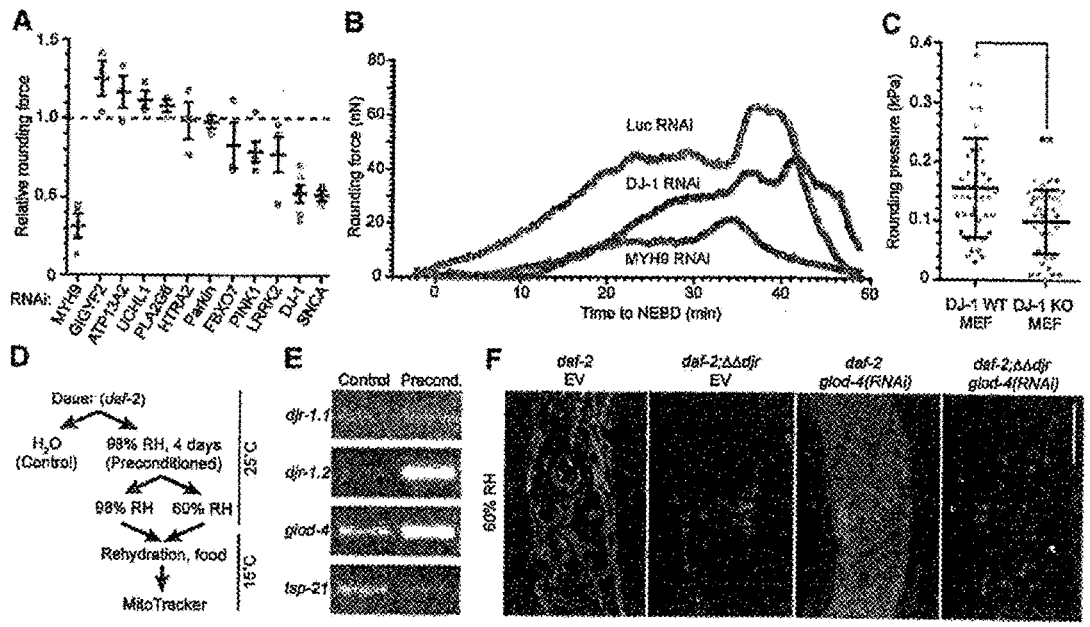
FIG. 1: DJ-1 is required for mitotic cell rounding and mitochondrial structure upon desiccation. (A) Mitotic rounding force of HeLa cells upon knocking down Parkinson's disease-related genes. Points indicate average cellular force of 12-18 cells normalized to Luciferase (Luc) control. Horizontal blue bars and error bars represent the mean of these values and the associated standard error of the mean, respectively. (B) Rounding force of esiRNA-treated HeLa cells during mitosis. n>4. (C) Rounding pressure of wild type (WT) and DJ-1 knock-out (KO) mouse embryonic fibroblasts (MEFs) throughout mitosis. Points represent individual measurements. Horizontal blue bars and error bars represent the mean and the standard deviation, respectively. **p<0.01. (D) Experimental procedure for preconditioning and rehydration of C. elegans dauer larvae. RH, relative humidity. (E) Differential expression of djr-1.1, djr-1.2, and glod-4 genes in the C. elegans dauer larva upon preconditioning. Tsp-21 gene was used as the internal control. (F) Disruption of the mitochondrial network upon desiccation and rehydration in daf-2ΔΔdjr dauer larvae treated with glod-4 RNAi. Scale bar, 10 μm.

The examples illustrate the invention.

Example 1—Materials and Methods

Cell Culture, RNAi, Worm Strains

HeLa-Kyoto cells stably expressing histone H2B-EGFP and mCherry-CAAX (clone 2B4), their parental cells, and HeLa-Kyoto expressing mouse DJ-1 transgene were used. Also, mouse embryonic fibroblast (MEF) (Pham et al., 2010) cells were used. Cells were maintained in DMEM supplemented with 10% fetal bovine serum (FBS), 2 mM GlutaMAX, 100 unit/ml penicillin, 100 μg/ml streptomycin, plus additional antibiotics for the transgene (0.5 mg/ml Geneticin for H2B-EGFP and mouse DJ-1 BAC transgene; 0.5 pug/ml puromycin for mCherry-CAAX), at 37° C. in a 5% $CO_2$ environment. The DMEM with high glucose (5 g/1) was used unless specifically mentioned (e.g. FIG. 14). For atomic force microscopy (AFM) measurements of mammalian cells, a $CO_2$-independent medium containing 4 mM sodium bicarbonate and 20 mM HEPES Was used. HeLa Cells Were RNAi-transfected with 160 nM endoribonuclease-digested small interfering RNA (MISSION esiRNA, Sigma) using oligofectamine reagent (Invitrogen). Paraquat ($PQ^{2+}$) was added 24 hours after RNAI. Cells were assayed after 48 hours from RNAI.

Worm Strains

All C. elegans strains were maintained on NGM agar plates seeded with Escherichia coli NA22 at 15° C. (Brenner, 1974). Mutant strains djr-1.1(tm918), djr-1.2 (tm951) and glod4(tm1266) were obtained from National Bioresource Project, Japan. Wild type (N2) and daf-2 mutant strains were obtained from Caenorhabditis Genetics Center, USA. All mutants were outcrossed at least twice. DJ-1 double mutant djr-1.1(tm918), djr-1.2(tm951), abbreviated as ΔΔdjr, was achieved by crossing both single mutants. This strain was then further crossed to daf-2 to generate daf-2; ΔΔdjr triple mutant.

Generation of DJ-1 Double Mutants

Outcrossed djr-1.1 and djr-1.2 males and hermaphrodites were crossed reciprocally. L4 hermaphrodites from $F_1$ generation were singled out and let lay eggs for 2 days. Subsequently, the adults were lysed and genotyped Individually.

One adult was put in 100 μl lysis buffer (1×PCR buffer and 200 ng/μl proteinase-K in water), snap-frozen in liquid nitrogen and incubated for 1 hour at 65° C. Then, the enzyme was denatured at 98° C. for 15 min. Genotyping PCR was performed in 1×PCR buffer with $MgCl_2$, 200 μM dNTP mix, 400 nM of each primer, 0.02 U Taq polymerase and 5 μl of gDNA from the lysis of an adult hermaphrodite using the following primers: tm918_ext_fwd: CGACGAGTTGCGTATGAGAA (SEQ D NO: 1), tm918_ext_rev CACAAGTTTTTTCGGGGAGAA (SEQ ID NO: 2), tm918_int_fwd TATGCCGGATTAGATGGAGC (SEQ ID NO: 3), tm951_ext_fwd GATTTCTTCGGCGTCTTCTG (SEQ ID NO: 4), tm951_ext_rev CACATCTCGGGCCAC-TATTT (SEQ ID NO: 5), tm951_int_fwd AAAATGCAAC-GACCGACTTC (SEQ ID NO: 6). PCR conditions were the following: initial denaturation at 94° C. for 10 min, amplification in 30 cycles of 94° C. for 30 sec, 62° C. for 25 sec and 72° C. for 30 Sec, final extension at 72° C. for 10 min.

Populations arising from an individual heterozygous for both alleles were selected and L4 hermaphrodites were singled out for one more round of genotyping as described above. Finally, 3 lines homozygous for both alleles were found. One of these lines was selected to be used in Subsequent experiments.

Genotyping of Glod-4(Tm1266) Mutants

After outcrossing with N2 twice, hermaphrodite L4s were singled out and genotyped as described above. The following primers were used: tm1266_ext_fwd TCCTC-CGCTCGCTTTTTCTC (SEQ ID NO: 7), tm1266_ext_rev TTGCAAGTTGCTTCGCATCC (SEQ ID NO: 8), tm1266_int_fwd TCGAAGCTTTGGTCGTTTCG (SEQ ID NO: 9). PCR conditions were the same as above, except that the annealing temperature was Increased to 65° C.

Preparation, Culture and Treatment of Primary Mesencephalic Dopaminergic Neurons from Mouse Embryos Primary mesencephalic neuronal cell cultures were prepared as previously described (Gille et al., 2004). Briefly, brain mesencephalons from E14.5 C57JBL6 or DJ-1 embryos were dissected under the microscope and digested with Trypsin-EDTA (Sigma-Aldrich). The trypsin reaction was stopped by adding the basic medium (BM) containing Neurobasal A medium (Gibco), 1 mg/ml penicillin/streptomycin, 10% (v/v) fetal calf serum (Invitrogen) and 2 mM L-glutamine and cells were mechanically dissociated using a fire-polished Pasteur pipette. Medium was fully replaced by centrifuging for 5 min. at 1200 rpm, aspirating the supernatant and adding 8 ml of the fresh BM to the pellet. Concentration of cells in the medium was estimated and cells were plated in a volume of 250 μl in 4-well plates (176740, Nunc, Thermo Scientific) or 35 pull in μ-clear 96-well plates (Greiner) coated with poly-D-lysine (Sigma-Aldrich) at a concentration of $2×10^6$ cells per ml. The same volume of medium containing the different treatment substances was added 4 hours after plating to obtain the following treatment concentrations: control, 3 mM glucose, 10 mM GA, 10 mMDL and 10 mM LL. 24 hours later ⅓ of the medium was replaced with fresh BM. On DIV3 (day-in-vitro-culture 3) half of the medium was replaced with B27 medium containing Neurobasal A medium, 1 mg/ml penicillin/streptomycin, 2 mM L-Glutamine (Sigma-Aldrich) and B-27 supplement (Life Technologies) and on DIV5 all medium was replaced by B27 medium. On DIV7 cell were either fixed using Accustain® (Sigma-Aldrich) for 30 min. or $PQ^{2+}$ treated at a concentration of 12.5 μM for 72 hours more and fixed.

Immunocytology of Mesencephalic Cell Cultures

Accustain® fixed neuronal cell cultures were washed 3×10 min in phosphate buffered saline (PBS), blocked using a blocking solution (BS) (0.2% Triton X-100 in PBS and 5% donkey serum (DS)) for 1 hour at RT, and incubated with mouse anti-TH (1:500, Millipore), chicken anti-βIII-tubulin (1:500, Millipore) and rabbit anti-TOM20 (1:200, FL-145, Santa Cruz Biotechnology) or rabbit anti-NeuN (1:500, Millipore) primary antibodies in BS overnight at 4 C. On the next day cells were washed 4×10 min with PBS, incubated in donkey Alexa® 488 anti-rabbit, donkey Alexa® 555 anti-mouse (Life Technologies) and donkey Alexa® 647-antichicken (Jackson ImmunoResearch) secondary antibodies for 1 hour at RT, washed 4×10 min. with PBS, incubated with Hoechst33342 for 10 min and washed once more in PBS.

Mitochondrial Live Staining of Worm Larva

Mitochondria staining was performed as previously described. Briefly, MitoTracker Deep Red or CMXROS (M22426, M7512, Life Technologies) were dissolved in DMSO at a concentration of 5 mM and kept at −20° C. as a stock solution. On the day of microscopy worms were incubated in a 1:1000 diluted MitoTracker for 45 min at room temperature. Worms were then paralyzed with 1 mM Levamizol (Sigma-Aldrich), placed on slides covered with a thin layer of NGM medium on top of which the coverslip (22×22 mm, Menzel-Glaser #1) was fixed using nail lack.

Chemicals

Glucose (Merck), glycolic acid (15451, ACROS Organics) neutralized with NaOH to pH=7.4, and sodium D-lactate (71716, Sigma), glyoxal (128465, Sigma), paraquat (sc-257968, SantaCruz biotechnologies or 36541 Fluka® from Sigma-Aldrich) were used. Other chemicals used in this study (e.g. FIG. 3A) are listed in the Table of FIG. 13.

Cell rounding pressure analysis with microcantilevers

Cells were grown on a glass-base dish (FD35, World Precision Instruments) with a silicon spacer, which was prepared from μ-Chamber 12 well (ibidi), in the center. Medium was replaced with the $CO_2$-independent medium, then the dish was mounted on the stage of a light microscope (AxioObserver Z1 or Axiovert200, Zeiss) equipped with a 20× objective (Plan Apochromat, NA=0.80). To measure the force of the mitotic cell, a tipless microcantilever (NSC12/CSC37-B with a nominal spring constant of 0.3 N/m, MikroMasch, Estonia) mounted on a glass block of the AFM head (NanoWizard I or II, JPK instruments, Berlin) was used. Setup and calibration were done before every experiment; see Stewart et al (Stewart at al., 2012) for the details of the procedures. In a quick force measurement illustrated in FIG. 5A, the cantilever was set at 14 m above the glass dish and moved over the mitotically arrested cells to measure the equilibrium force. Measuring the cellular force and pressure through mitosis was done as described (Stewart at al., 2012, Stewart at al., 2011). Otherwise the cell pressure and volume were measured in a constant-height assay, as illustrated in FIG. 5B: the cantilever was first set at 14 μm height and placed over a metaphase cell to record rounding force. The cantilever was then brought down to 8 μm height at 0.1 μmu/sec, to measure peak and equilibrium forces. The maximal cross-section area of the cell was measured from the DIC or mCherry-CAAX image to calculate cell pressure and volume. Calculation of cell pressure and volume, and the contact area to the Cantilever was done as described (Stewart et al., 2012; Stewart et al., 2011). In every experiment, RNAi penetrance was confirmed by lower pressure of MYH9 RNAI-treated cells (Toyoda at al., 2011).

Light Microscopy, and Image Analysis

To film the osmotically challenged HeLa cells, a DeltaVision system (Applied Precision) was used, equipped with an Olympus IX-71 Inverted microscope and a 40× (UPlanApo, NA=1.00) objective. Time-lapse images were acquired at 1-min intervals except during osmotic shock treatment (equal volume of water for hypotonic shock; equal volume of the AFM medium containing 2.86% (w/v) xylose for hypertonic shock). Deconvolved and maximally projected images were analyzed manually on Image.J to annotate the radius and the volume of the round objects (i.e. mitotic cells), assuming that the cells were spherical (Stewart et al., 2011). To image mitochondria of HeLa cells, MitoTracker Red CMXRos was added at 150 nM and fixed with 3% (w/v) paraformaldehyde in PBS, 1 mM $MgCl_2$, and 5 mM EGTA. Chromatin was counter-stained by 1 μg/ml Hoechst33342. They were imaged on the DeltaVision system using a 60× objective (PlanApo N, NA=1.42, Olympus), and deconvolved and maximally projected images were used for the analysis. Due to high background of MitoTracker in the center of the cell, mitochondria in a 15×15 um area in the periphery were manually annotated on Image.J software.

Microscopy images from live paralyzed worm larvae stained with MitoTracker were taken using a confocal microscope (LSM510, Zeiss, Germany). Samples were excited using a 514 (MitoTracker CMXRos) or a 647 (MitoTracker Deep Red) nm lasers and two channels, one BP505-550 or LP650 and the BF channel were used to acquire the images. Gain was maintained between 450 and 515 for all samples to ensure the detection of signal intensity differences.

Counting of Dopaminergic Neurons

Dopaminergic $TH^+$ neurons were observed using an inverted fluorescence microscope (Axiovert 200M, Zeiss) under a 10× objective (PlanApo, NA=0.45). The diameter of every well was scanned in two perpendicular directions (i.e. top to bottom and left to right) and total $TH^+$ neurons were counted for every well.

Immunoblotting

RNAi-transfected HeLa, MEFs, and mouse primary neurons were lysed in a lysis buffer (50 mM HEPES pH=7.5, 150 mM KC, 1 mM $MgCl_2$, 10% glycerol, 0.1% NP-40) with a protease inhibitor cocktail (Complete, Roche), resolved in SDS-PAGE, and transferred onto a nitrocellulose membrane. In immunoblotting, the following primary antibodies were used: human DJ-1 (FL-189, SantaCruz, 1:200 dilution); mouse DJ-1 (HPAO04190, Sigma, 1:250); GLO1 (FL-184, Santa Cruz, 1:200); alpha-tubulin (DM1A, Sigma, 1:2000). Horseradish peroxidase-conjugated anti-IgG antibodies (Bio-rad, 1:2000) were used for the secondary antibody. Chemiluminescence by ECL reagent was developed on a Hyperfilm (GE healthcare).

Measurement of ATP level, ATP:ADP ratio, and energy metabolism flux To measure ATP level in the cell lysate, a kit (A22066, Invitrogen) was used. Luminescence from the luciferase-luciferin reaction was measured on an automated reader (EnVision 2104, PerkinElmer). The luminescence was normalized using the protein amount in the samples. To measure the ATP:ADP ratio, cell extract was separated in an HPLC column essentially as described (Di Pierro et al., 1995). In short, HeLa cells were lysed in perchloric acid, cleared by centrifugation, neutralized by $K_2CO_3$, filtered with a 0.45 μm Millipore HV filter, and loaded onto a C-18 column (OOG-4252-E0, Phenomenex) connected to a HPLC system (Knauer). Absorption at 267 nm was used to calculate the relative abundance ratio of ATP and ADP.

Statistics and Graph Representation

Statistical differences between the treatments of the AFM measurements were determined by a non-parametric Mann-Whitney's U-test. For the other experiments, ANOVA followed by the Tukey's honestly significant differences post-hoc test. Data expressed in percentages were first transformed by Tukey's double arcsine function (Freeman and Tukey, 1950) to achieve normal distribution prior to ANOVA. Statistical analysis and graphs were done on a Prism software version 5 (GraphPad Inc.) and an R environment.

Example 2—Glycolate and D-lactate Support In Vitro and In Vivo Survival of Dopaminergic Neurons One of the genes associated with Parkinson's disease is DJ-1/PARK7, which belongs to a novel glyoxalase family (Lee et al., 2012). Glyoxalases are enzymes that transform 2-oxoaldehydes into corresponding 2-hydroxyacids, i.e. glyoxal and methylglyoxal into glycolate acid and D-lactate, respectively. Presently, two systems of glyoxalases have been described: 1) Glutathione-dependent GLO-1 and GLO-2 system (Thomalley, 2003) and 2) DJ-1/Glo III, that do not need a co-factor (Lee et al., 2012, Misra et al., 1995). Because substrates of glyoxalases are aggressive aldehydes produced by Oxidation of glucose during glycolysis (methylglyoxal) and peroxidation of fatty acids (glyoxal), it has been assumed that the major function of glyoxalases is to detoxify aldehyde by-products of metabolism (Thomalley, 2003). interestingly, this view was not always prevalent. Glyoxalases, and their corresponding products (e.g. D-lactate) were considered major components of glycolysis (Ray and Ray, 1998). With the elucidation of the now classic Embden-Meyerhof-Pamas pathway of glycolysis, production of D-lactate was seen more as an artifact of a biochemical procedure or an undesired side product of glycolysis. Thus, the cellular role of glyoxalases remains obscure.

One of the difficulties in understanding the precise function of DJ-1, is that DJ-1 knock-out mice have weak phenotypes. (Pham et al., 2010; Andres-Mateos et al., 2007; Kim et al., 2005). This is presumably because DJ-1 has minor effects on cell metabolism, which only appears with age. Generally, one of the problems in studying the role of a gene with minor defects in the metabolism, is that they likely to give rise to long term problems in cell survival, but have no phenotype in standard assays used by cell biologists studying cells in culture, for instance, cell division, or cell survival. Therefore it seems likely that novel assays, studying non-lethal phenotypes, will be necessary to study the function of such genes.

Figure 7:
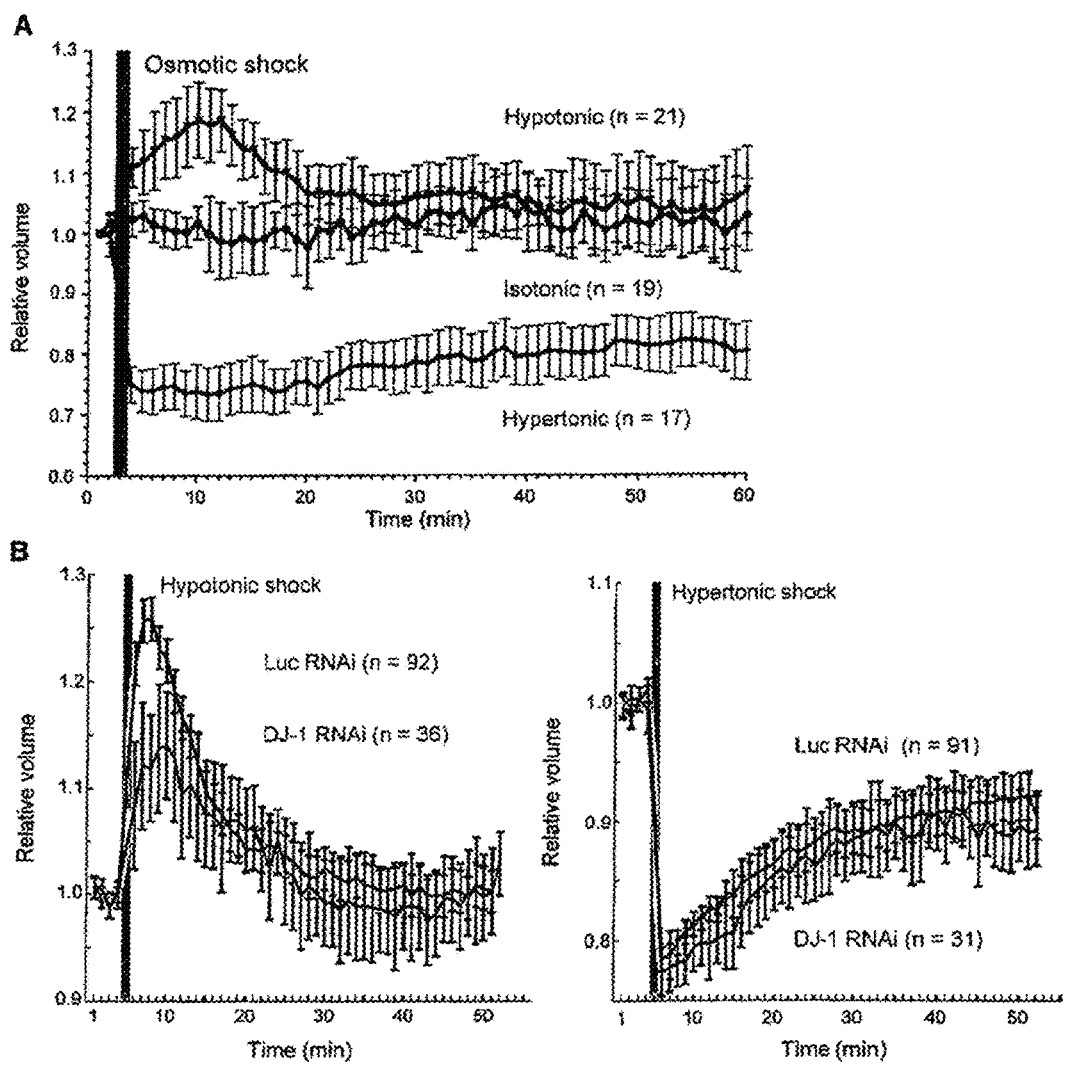
FIG. 7: DJ-1 is required for response to hypotonic shock during mitosis. (A) Volume change upon Osmotic shock. Mitotic HeLa cells arrested with S-trityl-L-cysteine (STC) were treated with the equal volume of the isotonic ($CO_2$-independent medium, 300 mOsm), hypotonic (distilled water), and hypertonic (2.86% (w/v) xylose, 500 mOsm) media after 4 min (gray vertical line). Then the volumes of mitotic cells were measured over time. Mean relative volumes (normalized to initial volume) with 95% confidence interval (CI) are shown. (B) Volume change of DJ-1-knockdown mitotic cells upon osmotic shock. Mitotically arrested, esiRNA-treated HeLa cells were treated with hypotonic (left panel) and hypertonic (right panel) media after 4 minutes (light blue or gray vertical lines, respectively). Then the volumes of the mitotic Cells were measured. Mean relative Volumes and 95% CIs are shown.

The opposed activity of osmotic pressure and acto-myosin contraction drive an increase in mechanical forces and cell rounding during mitosis (Stewart et al., 2011). In an ongoing screen for genes required for cell rounding, which takes place when cells prepare for mitosis (Stewart et al., 2011; Kunda and Baum, 2009, Cramer and Mitchison, 1997), it was found that silencing DJ-1 in HeLa cells resulted in reduced rounding force during metaphase, which was rescued by a DJ-1 transgene (FIG. 1A, B, FIG. 5D, E). It was also observed the same phenotype in DJ-1-deficient mouse embryonic fibroblasts (FIG. 1C, Supplementary FIG. 1F, G). These results were confirmed by monitoring the rounding pressure of cells as they proceed through mitosis (FIG. 5B, C). DJ-1-depleted mammalian cells had defects in response to hypotonic shock (FIG. 7), suggesting that they cannot exert rounding force because they cannot maintain their osmotic pressure. Inspired by these findings, a miniscreen was performed to test whether other Parkinson's disease-related genes are involved in the mechanics of cell rounding (FIG. 1A, FIG. 5A). Indeed, silencing of SNCA, PINK1, LRRK2, and FBXO7 genes significantly decreased mitotic cellular force. Therefore, genes involved in Parkinson's disease are in some way involved in cell rounding at mitosis.

Figure 6:
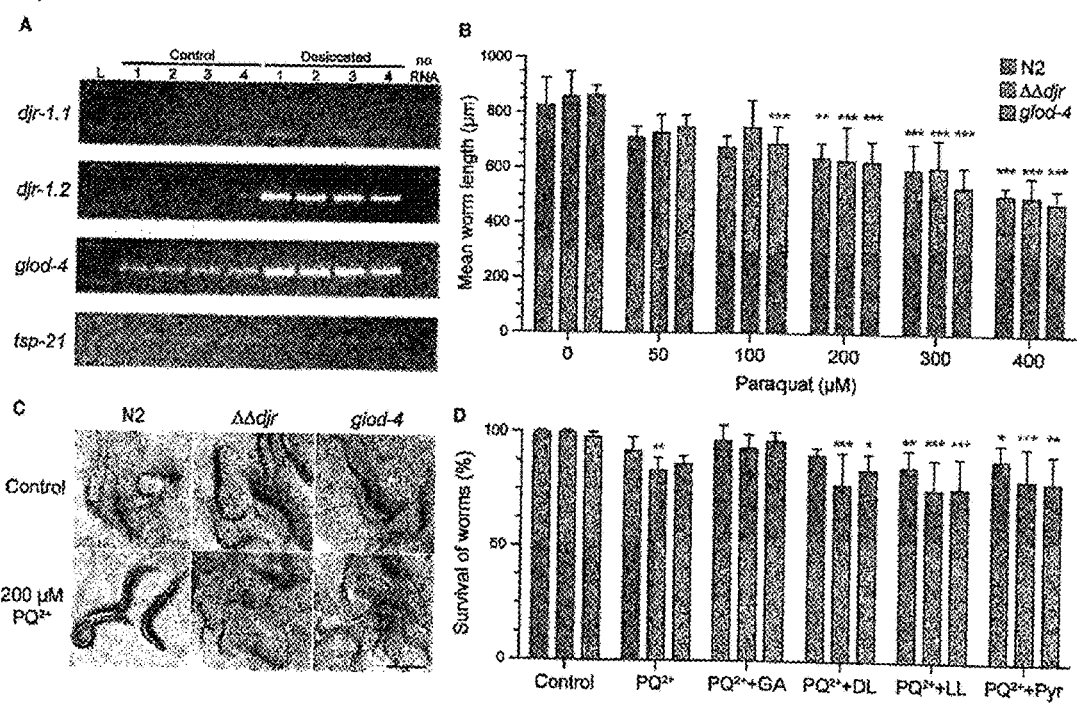
FIG. 6: Upregulation of glyoxalase genes upon desiccation of C. elegans dauer, and the effects of paraquat on worm larvae. (A) The differential expression of djr-1.1, djr-1.2 and glod-4 was tested by RT-PCR in four replicates. See FIG. 1d for the procedure. tsp-21 was a control whose expression did not change by desiccation stress. (B) Length of the worms treated with $PQ^{2+}$. Bars and error bars show the mean and SD, respectively. Sensitivity to $PQ^{2+}$ was comparable between strains (F=2.334, df=2, p=0.1) but overall increased by concentration (F=81,159, df=5, p<0.001). Every strain was compared to its control at different $PQ^{2+}$ concentrations by two-way ANOVA followed by Tukey's honestly significant differences (HSD) test. (C) Worm larvae treated with PQ or control. Scale bar, 250 μm. (D) survival of the worm larvae treated with 200 μM paraquat and 1 mM of the Indicated supplements. Bars and error bars show the mean and SD, respectively. Every strain was affected differently upon each treatment (strain level F=10.748, df=2, p<0.001; treatment level F=24.467, df=5, p<0.001). $PQ^{2+}$ decreased viability of ΔΔdjr mutant, which was restored by glycolate (GA), but not by D-lactate (DL), L-lactate (LL), or pyruvate (Pyr). Viability of glod-4 was not affected by $PQ^{2+}$ significantly, however the lethality was rescued in a similar way as ΔΔdjr. Every strain was compared to its own control by two-way ANOVA followed by Tukey's HSD test. Data were normalized by Freeman-Tukey's double arcsine transformation prior to ANOVA. *p<0.05; p<0.01; *p<0.001.

*Caenorhabditis elegans* dauer larva, an arrested stage specialized for survival in adverse conditions, is resistant to severe desiccation and can lose up to 98% of water (Erkut et al., 2011). However, this requires a preconditioning step at a mild desiccative environment to prepare the organism for harsher desiccation conditions. In a Screen to identify genes that are required for desiccation tolerance (Erkut et al., in press), it was found that expression of two DJ-1 orthologs dr-1.1, djr-1.2 were elevated during preconditioning (FIG. 1D, E, FIG. 6). The up-regulation of djr-1.2 was especially strong.

DJ-1 was recently reported to be a novel glyoxalase (Lee et al., 2012), a class of enzymes that are implicated in the detoxification of o-oxoaldehydes by converting them into a hydroxyacids (Thomalley, 2003). Glod-4, the only member of another glyoxalase family in *C. elegans*, was also up-regulated upon preconditioning (FIG. 1E, FIG. 6), suggesting the importance of glyoxalases for desiccation tolerance. Many genes involved in Parkinson's disease, among them DJ-1, have been linked to alterations in mitochondrial structure and function and an enhanced sensitivity to mitochondrial toxins like Complex-I inhibitors (Sal et al., 2012). Furthermore, many of the Parkinson's-linked genes that gave affected cell rounding are also involved in mitochondrial function (see FIG. 1A, FIG. 5C) (Burchell et al, 2013; Wang et al, 2012; Kamp et al, 2010 Irrcher et al, 2010: Clark et al. 2006: Park et al., 2006). The effect of glyoxalases was therefore tested on mitochondrial function/structure in worms. djr-1.1; djr-1.2 double mutant on daf-2(e1370ts) background were produced to produce dauer larvae defective in both DJ-1 homologs (daf-2; DDdjr). These worms were subjected to glod-4 RNAI for 2 generations to knockdown the entire glyoxalase pathway of the organism. Subsequently, dauers were preconditioned, desiccated, and rehydrated. Under these conditions, although desiccation tolerance was not obviously compromised, the elaborated network of mitochondria seen in daf-2 mutants, that were wild type for glyoxalase function, was almost non-existent in the triple mutant (FIG. 1D, F).

Figure 2:
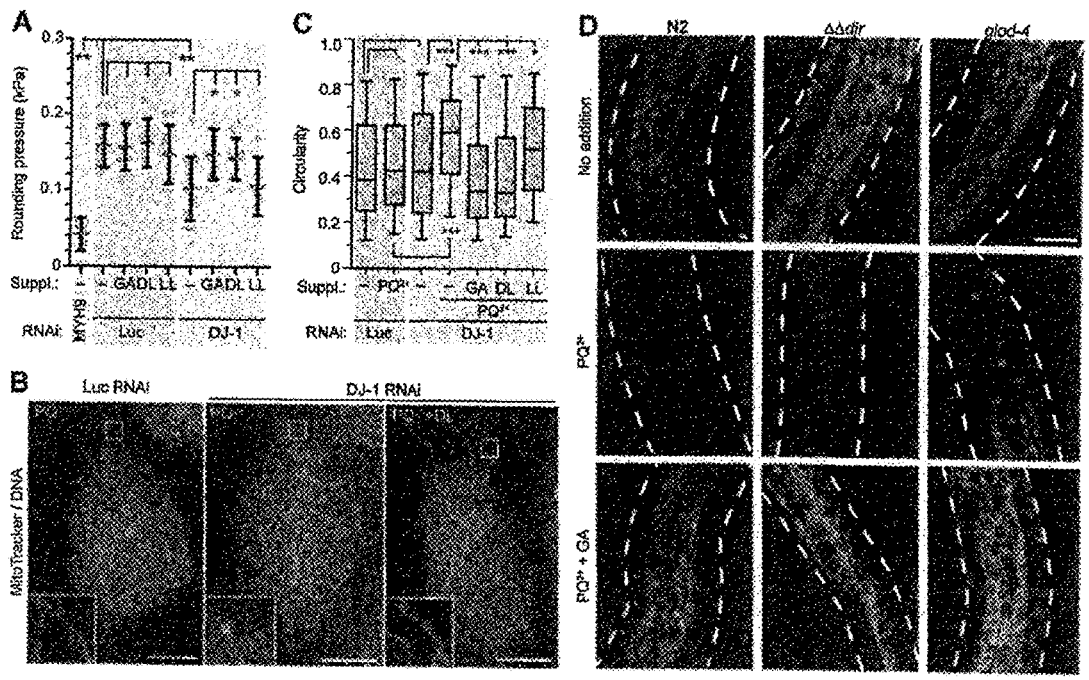
FIG. 2: Glycolate and D-lactate rescue phenotypes induced by loss of DJ-1 function. (A) Rounding pressure of mitotic RNA-treated HeLa cells in the presence of glycolate (GA), D-lactate (DL) and L-lactate (LL). Horizontal blue bars and error bars represent the mean and the standard deviation, respectively. *p<0.05; p<0.01, *p<0.001. (B) Mitochondria of paraquat ($PQ^{2+}$)-treated HeLa cells. Green, MitoTracker; Blue, DNA. inset, 4× magnification of the boxed area. (C) Circularity of mitochondria of HeLa cells. n≥280. (D) Mitochondria in worm glyoxalase mutants. Wild type (N2), DJ-1 mutant (ΔΔdjr) and GLOD-4 mutant (glod-4) were treated with $PQ^{2+}$ with or without GA, and stained with MitoTracker (red). Dashed lines show the outlines of larvae. Scale bars, 10 μm.
Figure 8:
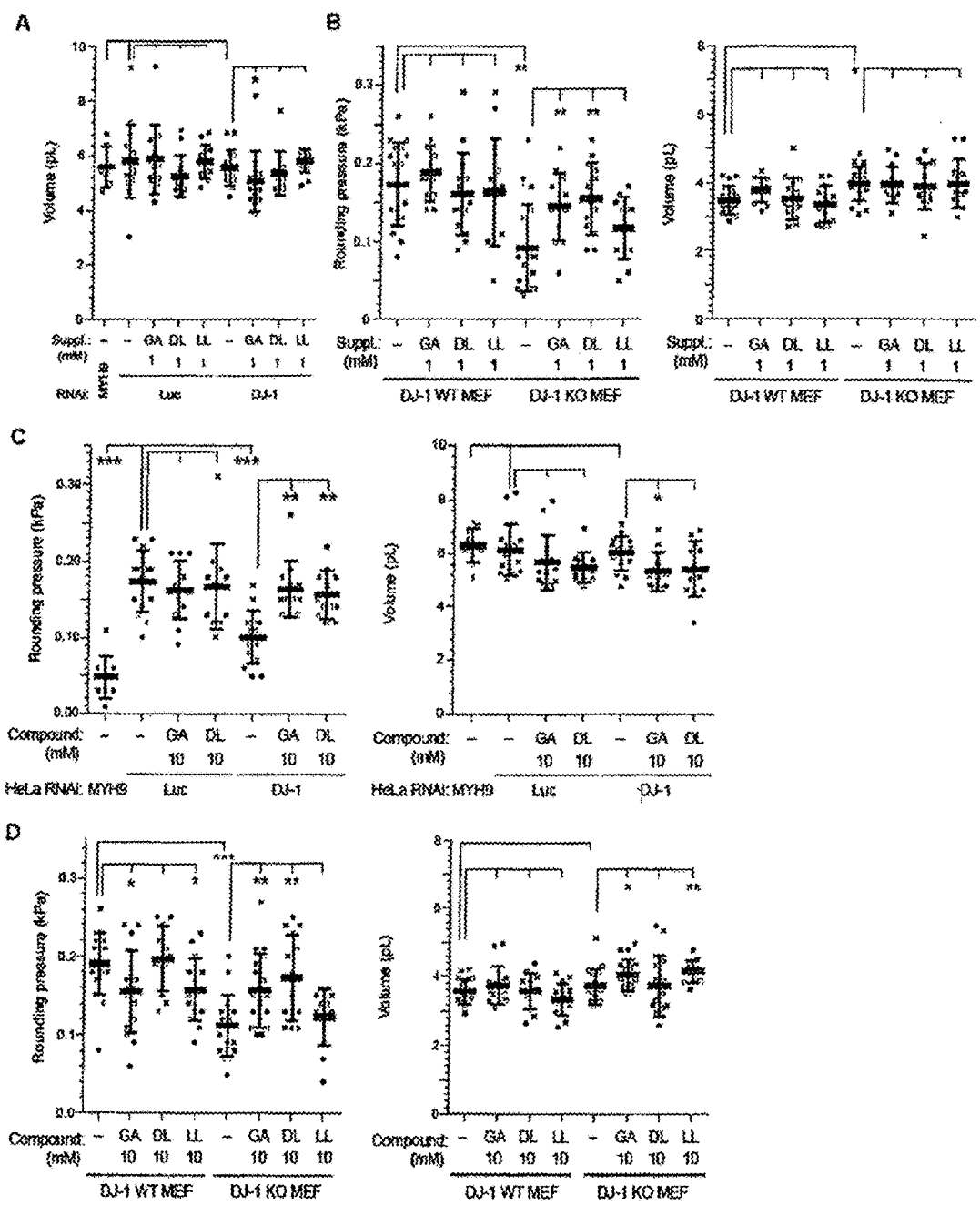
FIG. 8: Glycolate and D-lactate rescue the cell pressure defect of DJ-1-deficient mammalian cells. (A) Volume of metaphase RNA-treated HeLa cells supplemented with glycolate (GA), D-lactate (DL), and L-lactate (LL). Data of individual cells with the mean (blue) and SD are shown. Result is representative of three independent experiments. (B) Pressure (left) and volume (right) of mitotic MEF cells supplemented with GA, DL, and LL. Data of individual cells with the mean and SD are shown. *p<0.05; p<0.01; *p<0.001. (C-D) Rounding pressure (left) and volume (right) of RNAi-treated mitotic HeLa (C) and MEF (D) cells, in the presence of 10 mM glycolate (GA), D-lactate (DL), and L-lactate (LL). Cells were measured after 1 hour from addition of the supplement. Data of individual cells with mean and SD are shown. Like 1 mM of the supplements, 10 mM of GA and DL, but not LL, rescued the lower pressure phenotype. At 10 mM, GA and LL may have negative effects on cell mechanics as it decreases pressure of mitotic WT MEFs. *p<0.05; p<0.01; *p<0.001.

One possibility to explain the data so far presented is that the lack of glyoxalases could lead to the build up of their substrates, toxic aldehydes, leading to phenotypic alteration. However, another hypothesis is proposed herein: the defects may result not only from a build up of toxic aldehydes, but also from the lack of the enzymatic products themselves (a-hydroxyacids). To support this idea, it was looked at the effects of the products of glyoxalases, D-lactic acid (DL) and glycolic acid (GA) (Lee et al., 2012; Thomalley, 2003) on cell rounding. Indeed, it was shown that both DL and GA could rescue the reduced pressure of both mitotic DJ-1-RNAI cells and MEFs, whereas L-lactic acid (LL) had no effect (FIG. 2A, FIG. 8).

Figure 9:
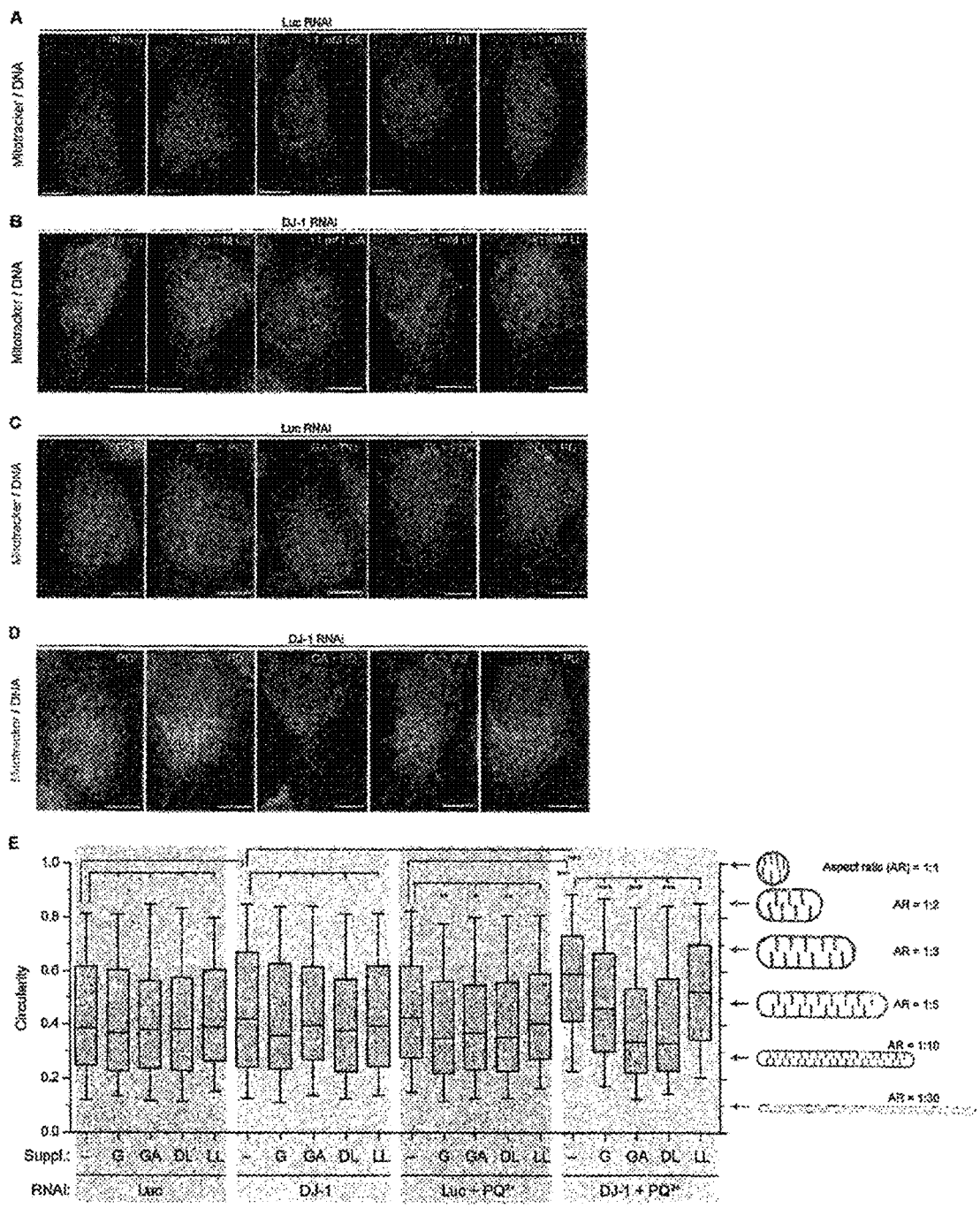
FIG. 9: Glucose, glycolate, D-lactate rescue mitochondria structure of DJ-1-depleted human cells. (A-D) Mitochondria (green) and DNA (blue) of cells treated with control RNAI (A), DJ-1 RNA (B), control RNAI and paraquat (PQ') (C), and DJ-1 RNAi and $PQ^{2+}$ (D). RNAi-treated cells were Incubated with the indicated supplements for 24 hours, stained with MitoTracker, and fixed. Note the round mitochondria in $PQ^{2+}$-treated DJ-1 RNAi cells without supplements. Scale bar, 10 μm. (E) Quantification of the disruption of mitochondrial network. Circularity of mitochondria in cell periphery was calculated (n>280 for each box). On the right, the relation between the mitochondrial shape and circularity is drawn. Circularity in each condition was compared to its own control by one-way ANOVA followed by Tukey's HSD test. *p<0.05; p<0.01; *p<0.001.

It was next looked whether products of glyoxalases are involved in maintenance of mitochondrial structure. DJ-1 RNAi in HeLa cells did not produce an altered mitochondrial phenotype (FIG. 2B). However, the addition of low doses of paraquat, an environmental poison known to affect mitochondria (Sal et al., 2012), and implicated in the onset of Parkinson's disease, disrupted mitochondrial structure in DJ-1 RNAI cells (FIG. 2B). Mitochondria became more circular, and this circular phenotype was rescued by addition of DL and GA (FIG. 2B, C, FIG. 9). A circular mitochondrial phenotype is common indicator of mitochondrial stress (Kanazawa et al., 2008). Similarly to human cells, paraquat disrupted mitochondria in reproductive larvae of *C. elegans*. In both a ΔΔdjr double mutant and a glod-4 single mutant background (FIG. 2D), paraquat resulted in circular mitochondria and diminished MitoTracker staining, and these alterations were reversed by addition of GA (FIG. 2D).

Figure 10:
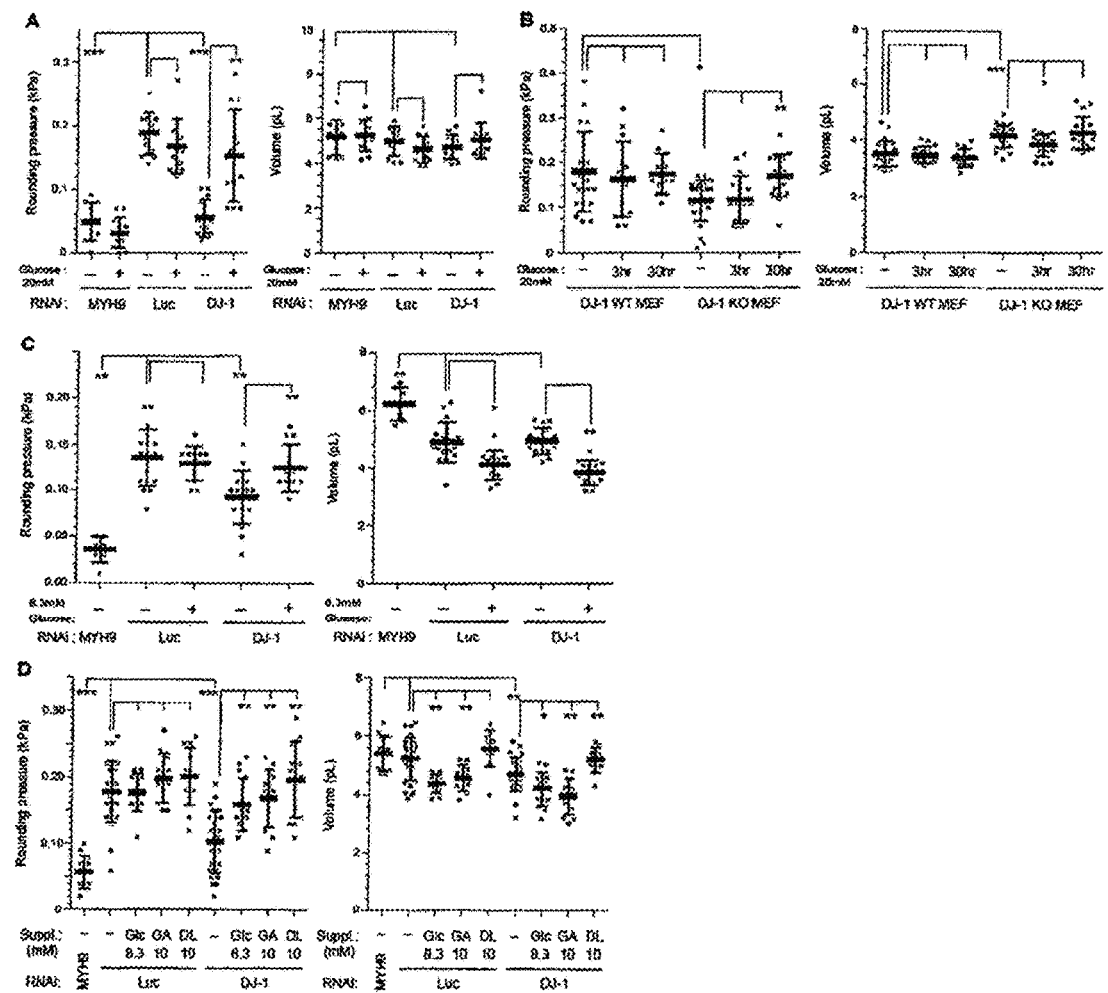
FIG. 10: Glucose rescues the lower pressure phenotype of mitotic DJ-1-depleted cells. (A) Rounding pressure and volume of the RNA-treated HeLa cells were measured before (−) and after (+) addition of 20 mM glucose. Note that glucose did not rescue the lower pressure of MYH9-RNAi cells. Data of individual cells with mean and SD are shown. p<0.01; *p<0.001. (B) Rounding pressure and volume of mitotic wild-type (WT) and DJ-1 knock-out (KO) MEFs. Glucose rescued the pressure defect of DJ-1 KO MEFs after a long incubation, but not within a few hours. Data of individual cells with mean and SD are shown. (C-D) Rounding pressure (left) and volume (right) of RNAi-treated metaphase cells in a low (C) or no (D) glucose medium, in the presence of glucose, glycolate (GA), and D-lactate (DL). HeLa cells were maintained for 2 or more passages in the low or no glucose medium before RNAi. Cells were measured after 1 hour since addition of the Supplement. Data of individual cells with mean and SD are shown. The rescue of the lower pressure phenotype was observed in both types of media. Results are representative of three independent experiments.

So far, it was shown that addition of products of glyoxalases can rescue some of the altered phenotype of DJ-1 mutations. Whether the endogenous pathways necessary for GA or DL production are essential can be analyzed using the mitotic cell-rounding assay, combined with silencing genes in mammalian metabolic pathways by RNAi (FIG. 3A). Remarkably, all tested genes that are known to be involved in generation of GA or DL were required for cell rounding. For example, silencing of glyoxalases, aldolases, triose phosphate isomerase, and D-lactate dehydrogenase decreased mitotic pressure (FIG. 3A, FIG. 13). However, RNAi of genes involved in glycogen metabolism, or ATP synthesis, had no effect on cell rounding. This suggests that DL and GA are indeed produced by metabolic pathways. Surprisingly, glucose alone could rescue the pressure defect of DJ-1 RNAi cells (FIGS. 9 and 10). This could be explained because glucose Increases ATP generation. However, neither pyruvate, which is produced from glucose, nor glutamine, which can enter the Krebs cycle, rescued the DJ-1 pressure phenotype (FIG. 3A, FIG. 14). Most probably, the role of rescuing the cell rounding phenotype is taken over by another glyoxalase, GLO1 (Thomrnalley, 2003). Indeed glucose failed to rescue the pressure phenotype in the cells in which both glyoxalases, DJ-1 and GLO1 were knocked-down, even under conditions in which GA and DL could rescue (FIG. 3C, FIG. 11). The latter finding shows that most GA and DL are derived from glycolysis.

Figure 4:
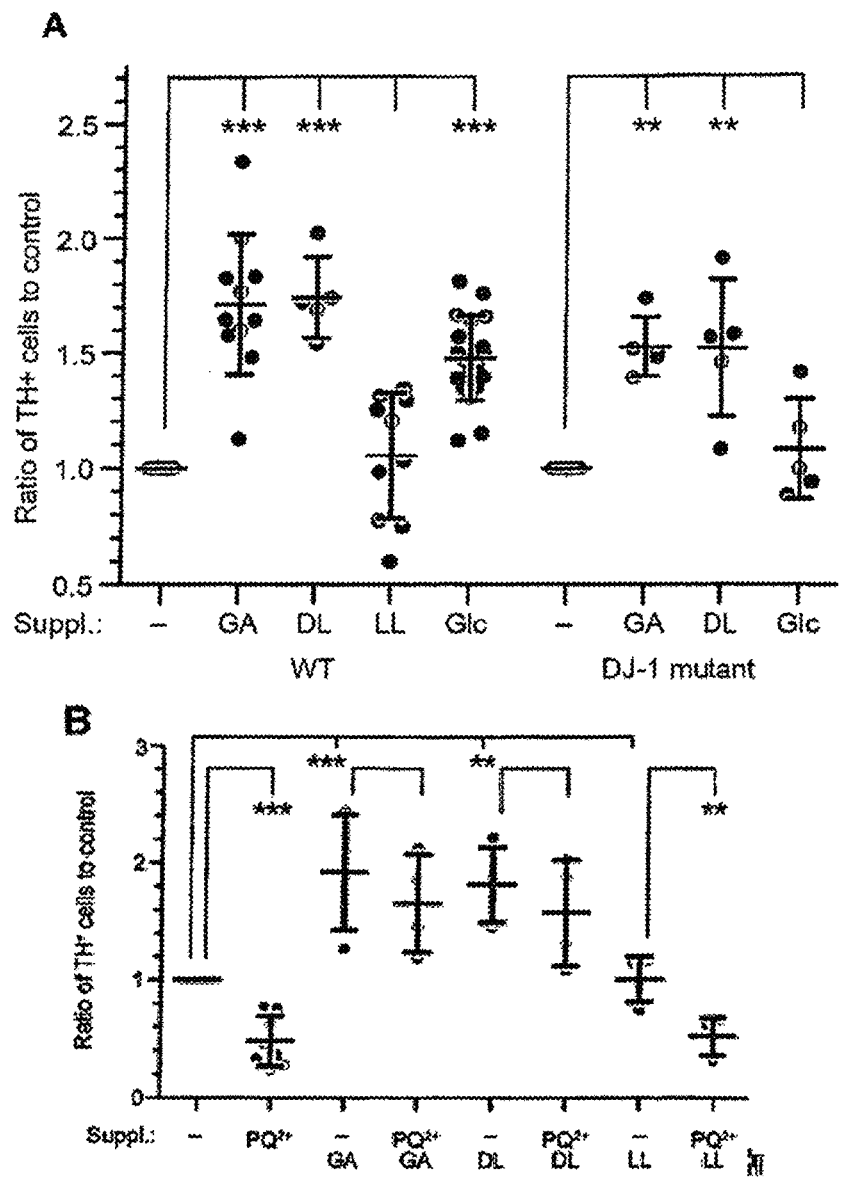
FIG. 4: Glycolate, D-lactate and glucose support viability of dopaminergic neurons in vitro. (A) Viability of the dopaminergic neurons in vitro from wild type and DJ-1 mutant mice embryos. Points show the ratio of tyrosine hydroxylase-positive (TH) cells to the control (no supplement). Horizontal blue bars and error bars represent the mean and the standard deviation, respectively. p<0.01, *p<0.001. (B) Viability of the dopaminergic neurons in the presence of 12.5 μM PQ' in the absence or presence of GA, DL, or LL. Primary neurons isolated from wild-type E14.5 embryos were cultured in vitro in the presence of the indicated supplements and $PQ^{2+}$. Points show the ratio of $TH^+$ cells to the control (no supplement). Horizontal blue bars and error bars represent the mean and the standard deviation, respectively.

Because toxins that affect mitochondrial function can hasten Parkinson's disease (Bove et al., 2005), it was questionable whether GA and DL would protect neurons against mitochondrial damage. Therefore, embryonic mesencephalic primary neuronal Cultures were generated and analyzed the Survival of tyrosine hydroxylase positive ($TH^{2+}$) neurons by immunostaining. Strikingly the in vitro survival of dopaminergic neurons was stimulated by glucose, GA, and DL, but not by LL (FIG. 4A). Furthermore, GA and DL significantly rescued the toxic effect of paraquat on neurons (FIG. 4B). It was also looked at the effect of these substances on dopaminergic neurons from DJ-1 knock out mice (FIG. 12). Again, GA and DL could stimulate neuronal survival. However, the positive effect of glucose on neuronal survival was dramatically diminished when using DJ-1 KO neurons. This suggests that, in dopaminergic neurons lacking DJ-1, GA and DL cannot be produced from glucose. These results stress the importance of GA and DL in survival of dopaminergic neurons.

The importance of the glyoxalases is supported by the fact that cells have two different glyoxalase systems. The overlapping phenotypes of the different glyoxalase systems have not been extensively studied. However, DJ-1 is up-regulated in aged mice (Jain et al., 2012), while the activity of Worm GLOD-4 in *C. elegans* decreases over aging (Morcos et al., 2008). Therefore DJ-1 may be more critical in protection from aging-derived stress. Indeed, glucose failed to support dopaminergic neuron survival in the DJ-1 mutant background (FIG. 4A), suggesting that DJ-1 is the primary glyoxalase in the mammalian central nervous system. This also may explain why mutations in DJ-1 cause neuron-specific diseases in humans.

The data herein highlight an understudied aspect of the Embden-Meyerhof glycolytic pathway, which is that a small fraction of triose-phosphate is converted into methyiglyoxal, which is further transformed into D-lactate by glyoxalases (Thornalley, 2003). This D-lactate-producing flux could protect mitochondria of diverse cells from environmental and metabolic stresses. To date it has been thought that glyoxalases protect cells by removing products of glycolysis or lipid oxidation. Thus, the experimental data herein suggests that glyoxalases have two functions: on one hand they detoxify chemically aggressive aldehydes and on the other hand they produce compounds necessary for cell physiology.

Without wishing to be bound by theory the Working hypothesis is that the glyoxalase systems are required to protect mitochondria from stress. It is concluded that increased rounding force as cells enter mitosis, response to osmotic shock, and in vitro culture of primary dopaminergic neurons, are conditions that induce mitochondrial stress. It is not understood how D-lactate, or glycolate protect mitochondria. It is well accepted that the dye that was used to follow mitochondria, MitoTracker, detects the potential of the mitochondrial membrane, which is required for most mitochondrial functions. It therefore seems likely that GA and DL in some way are involved in maintaining mitochondrial potential, which in turn is related to the network structure of mitochondria. GA and DL may act via a role in signaling, or as cofactors in the activity of enzymes or structural proteins necessary for mitochondrial function.

In addition to their role in maintaining mitochondrial health under stress, it is noted that DJ-1 and its products are Involved in two different processes that involve changes in osmotic pressure: Cell rounding at mitosis, and response to desiccation stress. Because cell rounding requires the generation of osmotic pressure (Stewart et al., 2011), it seems probable that DJ1 mutant cells cannot generate cell force in mitosis because they cannot maintain their osmotic pressure. It also seems likely that response to desiccation involves regulation of osmotic pressure. It will be Interesting to understand whether altered osmotic pressure is directly linked to mitochondrial stress or the products of glyoxalases have two independent functions. There are indications that these processes could be interconnected: Glyoxalases are up-regulated under osmotic stress in yeast (Inoue at al., 1998), and osmotic stress has been shown to reduce the mitochondrial membrane potential (Desai et al., 2002). Thus it is possible that the symptoms of Parkinson's disease, neuronal cell death in the substantia nigra, arise from an increased sensitivity of dopaminergic neurons to continuous osmotic stress (Federico et al., 2012, Corti et al., 2011), which is in turn linked to a decline in mitochondrial activity.

REFERENCES

Burchell V S, Nelson D E, Sanchez-Martinez A, Delgado-Camprubi M, Ivatt R M, Pogson J H, et al. 2013. The Parkinson's disease-linked proteins Fbxo7 and Parkin Interact to mediate mitophagy. *Nat Neurosci* 16: 1257-65. doi: 10.1038/nn.3489

Goedert M., Spillantini M G, Del Tredici K, and Braak H. 2013. 100 years of Lewy pathology. *Nat Rev Neurol* 9: 13-24. doi: 10. 1038/nmeuro.2012.242

Braidy N, Gai W P, Xu Y H, Sachdev P, Guillemin G J, Jiang X M, et al. 2013. Alpha-Synuclein Transmission and Mitochondrial Toxicity in Primary Human Foetal Enteric Neurons in Vitro. *Neurotox Res*.doi: 10. 1007/S 12640-013-9420-5

Schapira A H. 2012. Mitochondrial diseases. Lancet 379: 1825-34. doi:10.1016/S01406736(11)61305-6

Federico A, Cardaioli E, Da Pozzo P, Formichi P, Gallus G N, and Radi E. 2012. Mitochondria, oxidative stress and neurodegeneration. *J Neurol Sci* 322: 254-62. doi:10.1016/1.ijns.2012.05.030

Sai Y, Zou Z, Peng K, and Dong Z. 2012. The Parkinson's disease-related genes act in mitochondrial homeostasis. *Neurosci Biobehav Rev.* 36: 2034-43. doi: 10.1016/j.neubiorev.2012.06.007

Freire C, and Koifman S. 2012. Pesticide exposure and Parkinson's disease: epidemiological evidence of association. *Neurotoxicology* 33: 947-71. doi:10.1016/j.neuro.2012.05.011

Lee J Y, Song J, Kwon K, Jang S, Kim C, Baek K, et al. 2012. Human DJ-1 and its homologs are novel glyoxalases. *Hum Mol Genet* 21: 3215-25. doi:10.1093/hmg/dds155

Wang X, Yan M H, Fujioka H, Liu J, Wilson-Delfosse A, Chen S G, et al. 2012. LRRK2 regulates mitochondrial dynamics and function through direct interaction with DLP1. *Hum Mol Genet* 21: 1931-44. doi:10.1093/hmg/dds003

Stewart M P, Toyoda Y, Hyman A A, and Muller D J. 2012. Tracking mechanics and volume of globular cells with atomic force microscopy using a constant-height clamp. *Nat Protoc* 7: 143-54. doi:10.1038/nprot. 2011.434

Jain D, Jain R, Eberhard D, Eglinger J, Bugliani M, PiemontiL, et al. 2012. Age- and dietdependent requirement of DJ-1 for glucose homeostasis in mice with implications for human type 2 diabetes. *J Mol Cell Biol.* 4: 221-30. doi: 10.1093/mcb/mjs025

Pan-Montojo F, Schwarz M, Winkler C, Arnhold M, O'Sullivan G A, Pal A, et al. 2012. Environmental toxins trigger PD-like progression via increased alpha-synuclein release from enteric neurons in mice. *Sci Rep* 2: 898. doi:10.1038/srep00898

Stewart M P, Helenius J, Toyoda Y, Ramanathan S P, Muller D J, and Hyman A A. 2011. Hydrostatic pressure and the actomyosin cortex drive mitotic cell rounding. *Nature* 469: 226 30. doi:10.1038/nature09642

Corti O, Lesage S, and Brice A. 2011. What genetics tells us about the causes and mechanisms of Parkinson's disease. *Physiol Rev* 91: 1161-218. doi: 10.1152/physrev.00022.2010

Toyoda Y, Stewart M P, Hyman A A, and Muller D J. 2011. Atomic Force Microscopy to Study Mechanics of Living Mitotic Mammalian Cells. *Japanese Journal of Applied Physics* 50: 1-6. doi: 10.1143/JJAP. 50.08 LA01

Erkut C, Penkov S, Khesbak H, Vorkel D, Verbavatz J M, Fahmy K, et al. 2011. Trehalose renders the dauer larva of *Caenorhabditis elegans* resistant to extreme desiccation. *Curr Biol* 21: 1331-6. doi:10.1016/j.cub.2011.06.064

Kamp F, Exner N, Lutz A K, Wender N, Hegermann J, Brunner B, et al. 2010. Inhibition of mitochondrial fusion by alpha-synuclein is rescued by PINK1, Parkin and DJ-1. *Embo J* 29: 3571-89. doi:10.1038/emboj.2010.223

Irroher I, Aleyasin H, Sefert E L, Hewitt S J, Chhabra S, Phillips M, et al. 2010. Loss of the Parkinson's disease-linked gene DJ-1 perturbs mitochondrial dynamics. *Hum Mol Genet* 19: 3734-46. doi:10.1093/hmg/dda288

Pham T T, Giesert F, Rothig A, Floss T, Kallnik M, Weindl K, et al. 2010. DJ-1-deficient mice show less TH-positive neurons in the ventral tegmental area and exhibit non-motoric behavioural impairments. *Genes Brain Behav* 9: 305-17. doi:10.1111/j.1601-183X.2009.00559.x Kunda P, and Baum B. 2009. The actin cytoskeleton in spindle assembly and positioning. *Trends Cell Biol* 19: 174-9. doi:10.1016/j.tcb.2009.01.006

Morcos M, Du X, Pfisterer F, Hutter H, Sayed A A, Thomalley P, et al. 2008. Glyoxalase-1 prevents mitochondrial protein modification and enhances lifespan in *Caenorhabditis elegans*. *Aging Cell* 7:260-9, doi:10.1111/j. 1474-9726.2008.00371.x Kanazawa T, Zappaterra M D, Hasegawa A, Wright A P, Newman-Smith E D, Buttle K F, et al. 2008. The C. elegans Opa1 homologue EAT-3 is essential for resistance to free radicals. *PLoS Genet* 4: e1000022. doi:10.1371/journal.pgen.1000022

Andres-Mateos E, Perler C, Zhang L, Blanchard-Fillion B, Greco T M, Thomas B, et al. 2007. DJ-1 gene deletion reveals that DJ-1 is an atypical peroxiredoxin-like peroxidase. *Proc Natl Acad Sci USA* 104: 14807-12. doi:10.1073/pnas.0703219104

Clark I E, Dodson M W, Jiang C, Cao J H, Huh J R, Seol J H, et al. 2006. *Drosophila* pink 1 is required for mitochondrial function and interacts genetically with parkin. *Nature* 441: 1162-6.doi: 10.1038/nature04779

Park J, Lee S B, Lee S, Kim Y, Song S, Kim S, et al. 2006. Mitochondrial dysfunction in *Drosophila* PINK1 mutants is complemented by parkin. *Nature* 441: 1157-61. doi: 10.1038/nature04788

Kittler R, Pelletler L, Ma C, Poser, Fischer S, Hyman A A, et al. 2005. RNA interference rescue by bacterial artificial chromosome transgenesis in mammalian tissue culture cells. *Proc Natl Acad Sci USA* 102: 2396-401. doi: 10.1073/pnas.0409861102

Kim R H, Smith P D, Aleyasin H, Hayley S, Mount M P, Pownall S, et al. 2005. Hypersensitivity of DJ-1-deficient mice to 1-methyl-4-phenyl-1,2,3,6-tetrahydropyrindine (MPTP) and oxidative stress. *Proc Natl Acad Sci USA* 102:5215-20. doi:10.1073/pnas.0501282102

Bove J, Prou D, Perier C, and Przedborski S. 2005. Toxin-induced models of Parkinson's disease. *NeuroRX* 2: 484-94. doi:10.1602/neurorx.2.3.484

Gille G, Hung S T, Reichmann H, and Rausch W D. 2004. Oxidative stress to dopaminergicneurons as models of Parkinson's disease. *Ann N Y Acad Sci* 1018: 533-40. doi: 10.1196/annals.1296.066

Song D D, Shults C W, Sisk A, Rockenstein E, and Masliah E. 2004. Enhanced substantia nigra mitochondrial pathology in human alpha-synuclein transgenic mice after treatment with MPTP. *Exp Neurol* 186: 158-72. doi:10.1016/S0014-4886(03)00342-X Bonifati V, Rizzu P, van Baren M J, Schaap O, Breedveld G J, Krieger E, et al. 2003. Mutations in the DJ-1 gene associated with autosomal recessive early-Onset parkinsonism. *Science* 299: 256-9. doi:10.1126/science. 1077209

Thomalley P J. 2003. Glyoxalase 1-structure, function and a critical role in the enzymatic defence against glycation. *Biochem Soc Trans* 31: 1343-8. doi:10.1042/

Desai B, Myers BR, and Schreiber SL. 2002. FKBP12-rapamycin-associated protein associates with mitochondria and senses osmotic stress via mitochondrial dysfunction. *Proc Natl Acad Sci USA* 99: 4319-24. doi:10.1073/pnas.261702698

Inoue Y, Tsujimoto Y, and Kimura A. 1998. Expression of the glyoxalase I gene of *Saccharomyces cerevisiae* is regulated by high osmolarity glycerol mitogen-activated protein kinase pathway in osmotic stress response. *J Biol Chem* 273:2977-83.

Ray M, and Ray S. 1998. Methylglyoxal: From a putative intermediate of glucose breakdown to its role in understanding that excessive ATP formation in cells may lead to malignancy. *Current Science* 75: 103-13.

Nagakubo D, Taira T, Kitaura H, Ikeda M, Tamai K, Iiguchi-Ariga S M, et al. 1997. DJ-1, a novel oncogene which transforms mouse NIH3T3 cells in cooperation with ras. *Biochem Biophys Res Commun* 231:509-13. doi: 10.1006/bbrc. 1997.6132

Cramer L P, and Mitchison T. J. 1997. Investigation of the mechanism of retraction of the cell margin and rearward flow of nodules during mitotic cell rounding. *Mol Biol Cell* 8: 109-19.

Misra K, Banerjee A B, Ray S, and Ray M. 1995. Glyoxalase III from *Escherichia coli*: a single novel enzyme for the conversion of methylglyoxal into D-lactate without reduced glutathione. *Biochem J* 305 (Pt 3): 999-1003.

Di Pierro D, Tavazzi B, Pemo C F, Bartolini M, Balestra E, Calio R, et al. 1995. An ion-pairing high-performance liquid chromatographic method for the direct simultaneous determination of nucleotides, deoxynucleotides, nicotinic coenzymes, Oxypurines, nucleosides, and bases in perchloric acid cell extracts. *Anal Biochem* 231: 407-12. doi:10.1006/abio, 1995.0071

Schapira A H, Cooper J M, Dexter D, Jenner P, Clark J B, and Marsden C D. 1989. Mitochondrial complex deficiency in Parkinson's disease. *Lancet* 1: 1269.

Brenner S. 1974. The genetics of *Caenorhabditis elegans*. *Genetics* 77: 71-94.

Freeman M F, and Tukey J W. 1950. Transformations Related to the Angular and the Square Root. *Ann Math Statistics* 21:607-11 doi:10.1214/aoms/11777297.56

---

The invention claimed is:

1. A method of treatment of a neurodegenerative disease which is associated with a decline in mitochondrial activity, said method comprising administering to a person in need of such treatment for a neurodegenerative disease with decline in mitochondrial activity, a therapeutically effective amount of glycolic acid or a pharmaceutically acceptable salt thereof, and optionally D-lactic acid or a pharmaceutically acceptable salt or ester thereof.

2. The method of claim 1, wherein said disease is selected from the group consisting of Parkinson's disease, Alzheimer's disease, Huntington's disease, Amyotrophic lateral sclerosis, and other neurodegenerative diseases.

3. The method of claim 2, wherein the disease is Parkinson's disease.

4. The method of claim 1, wherein the glycolic acid or a pharmaceutically acceptable salt thereof, and the D-lactic acid or a pharmaceutically acceptable salt or ester thereof are comprised in a formulation, said formulation containing
   (i) glycolic acid or a pharmaceutically acceptable salt thereof, in an amount of at least 0.005% (w/w), and
   (ii) D-lactic acid or a pharmaceutically acceptable salt or ester thereof in an amount of at least 1.0% (w/w).

5. The method of claim 1, further comprising administering pyruvate to said person.

6. The method of claim 1, further comprising administering one or more antioxidants to said person.

7. The method of claim 6, where the antioxidants comprise coenzyme Q10.

8. The method of claim 1, further comprising administering one or more vitamins to said person.

9. The method of claim 8, wherein said one or more vitamins are selected from the group consisting of vitamin E, C, B2 and B9.

10. The method of claim 1, further comprising administering one or more compounds selected from the group consisting of L-arginine, L-carnitine and L-creatine to said person.

11. The method of claim 1, wherein the glycolic acid or the pharmaceutically acceptable salt thereof, or the D-lactic acid or the pharmaceutically acceptable salt or ester thereof is formulated as a medical food or medical food supplement.

12. The method of claim 11, wherein the medical food or medical food supplement is a milk-based medical food or milk-based medical food supplement.

* * * * *